United States Patent
Min

(10) Patent No.: US 7,881,787 B1
(45) Date of Patent: Feb. 1, 2011

(54) CAPTURE DETECTION SYSTEM AND METHOD CRT THERAPY

(75) Inventor: Xiaoyi Min, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 964 days.

(21) Appl. No.: 11/612,239

(22) Filed: Dec. 18, 2006

(51) Int. Cl.
*A61N 1/00* (2006.01)
(52) U.S. Cl. .......................................... 607/9
(58) Field of Classification Search ................. 600/510, 600/520; 607/9, 14, 23, 25, 28
See application file for complete search history.

(56) References Cited

U.S. PATENT DOCUMENTS

| | | | |
|---|---|---|---|
| 4,712,555 A | 12/1987 | Thornander et al. | |
| 4,788,980 A | 12/1988 | Mann et al. | |
| 4,928,688 A | 5/1990 | Mower | |
| 4,940,052 A | 7/1990 | Mann et al. | |
| 4,944,298 A | 7/1990 | Sholder | |
| 5,086,774 A | 2/1992 | Duncan | |
| 5,174,289 A | 12/1992 | Cohen | |
| 5,179,949 A | 1/1993 | Chirife | |
| 5,391,189 A | 2/1995 | van Krieken et al. | |
| 5,466,254 A | 11/1995 | Helland | |
| 5,476,483 A | 12/1995 | Bornzin et al. | |
| 5,643,327 A | 7/1997 | Dawson et al. | |
| 5,741,308 A | 4/1998 | Sholder | |
| 5,749,906 A | 5/1998 | Kieval et al. | |
| 5,800,465 A | 9/1998 | Thompson et al. | |
| 5,814,077 A | 9/1998 | Sholder et al. | |
| 5,873,895 A | 2/1999 | Sholder et al. | |
| 6,122,546 A | 9/2000 | Sholder et al. | |
| 6,141,588 A | 10/2000 | Cox et al. | |
| 6,144,880 A | 11/2000 | Ding et al. | |
| 6,148,234 A * | 11/2000 | Struble ........................ | 607/28 |
| 6,285,907 B1 | 9/2001 | Kramer et al. | |
| 6,314,323 B1 | 11/2001 | Ekwall | |
| 6,360,127 B1 | 3/2002 | Ding et al. | |
| 6,411,848 B2 | 6/2002 | Kramer et al. | |
| 6,424,865 B1 | 7/2002 | Ding | |
| 6,473,645 B1 | 10/2002 | Levine | |
| 6,473,647 B1 | 10/2002 | Bradley | |
| 6,496,730 B1 | 12/2002 | Kleckner et al. | |
| 6,512,953 B2 * | 1/2003 | Florio et al. ................... | 607/28 |

(Continued)

FOREIGN PATENT DOCUMENTS

EP  0494487 B1  1/1996

(Continued)

OTHER PUBLICATIONS

Merino, J.L. MD et al., "Bundle-Branch Reentry and the Postpacing Interval After Entrainment by Right Ventricular Apex Stimulation," Circulation (2001), pp. 1102-1108.

(Continued)

*Primary Examiner*—George Manuel
*Assistant Examiner*—Robert N Wieland

(57) ABSTRACT

An exemplary method includes implementing a cardiac pacing therapy capable of delivering bi-ventricular stimulation, deciding if the therapy calls for bi-ventricular stimulation and, if the therapy calls for bi-ventricular stimulation, comparing an interventricular conduction delay to a threshold and based on the comparing, deciding whether to enable a capture detection algorithm. Various other exemplary methods, devices, systems, etc. are also disclosed.

17 Claims, 22 Drawing Sheets

U.S. PATENT DOCUMENTS

| | | | |
|---|---|---|---|
| 6,567,700 | B1 | 5/2003 | Turcott et al. |
| 6,606,516 | B2 | 8/2003 | Levine |
| 6,622,040 | B2 | 9/2003 | Ding et al. |
| 6,668,194 | B2 | 12/2003 | VanHout |
| 6,754,530 | B2 | 6/2004 | Bakels et al. |
| 6,804,555 | B2 * | 10/2004 | Warkentin ............... 607/9 |
| 6,934,586 | B2 | 8/2005 | Struble et al. |
| 6,959,214 | B2 | 10/2005 | Pape et al. |
| 6,961,613 | B2 * | 11/2005 | Bjorling et al. ............ 607/9 |
| 7,203,541 | B2 | 4/2007 | Sowelam et al. |
| 2001/0016759 | A1 | 8/2001 | Kramer et al. |
| 2001/0031993 | A1 | 10/2001 | Salo et al. |
| 2001/0049542 | A1 * | 12/2001 | Florio et al. ............. 607/28 |
| 2002/0049478 | A1 | 4/2002 | Ding et al. |
| 2002/0062139 | A1 | 5/2002 | Ding |
| 2002/0077559 | A1 | 6/2002 | Ding et al. |
| 2002/0161410 | A1 | 10/2002 | Kramer et al. |
| 2002/0177879 | A1 | 11/2002 | Ding et al. |
| 2003/0004548 | A1 | 1/2003 | Warkentin |
| 2003/0014084 | A1 | 1/2003 | VanHout |
| 2003/0060851 | A1 | 3/2003 | Kramer et al. |
| 2003/0130702 | A1 | 7/2003 | Kramer et al. |
| 2003/0195580 | A1 | 10/2003 | Bradley et al. |
| 2003/0204212 | A1 | 10/2003 | Burnes et al. |
| 2004/0133246 | A1 | 7/2004 | Ding et al. |
| 2004/0147966 | A1 | 7/2004 | Ding et al. |
| 2004/0193223 | A1 | 9/2004 | Kramer et al. |
| 2005/0090870 | A1 | 4/2005 | Hine et al. |
| 2005/0149138 | A1 * | 7/2005 | Min et al. ............... 607/27 |
| 2006/0149328 | A1 * | 7/2006 | Parikh et al. ............ 607/28 |
| 2008/0065166 | A1 * | 3/2008 | Sathaye et al. ........... 607/28 |

FOREIGN PATENT DOCUMENTS

| | | |
|---|---|---|
| EP | 1199085 A2 | 4/2002 |
| EP | 1234597 A2 | 8/2002 |
| WO | WO99/58191 | 11/1999 |
| WO | 02051495 A2 | 7/2002 |
| WO | 03037427 A1 | 5/2003 |
| WO | WO03/037427 A1 | 5/2003 |
| WO | 2005039690 A1 | 5/2005 |

OTHER PUBLICATIONS

Nelson, G.S. PhD. et al., "Left Ventricular or Biventricular Pacing Improves Cardiac Function at Diminished Energy Cost in Patients with Dilated Cardiomyopathy and left Bundle-Branch Block," Circulation (2000), pp. 3053-3059.

Gerber, T.C. MD et al., "Left Ventricular and Biventricular Pacing in Congestive Heart Failure," Mayo Clinic Proc. (2001), vol. 76, pp. 803-812.

Wang, Paul et al., "Timing Cycles for Biventricular Pacing," PACE, 2002; vol. 25(1), pp. 62-75.

Final Office Action, mailed Jul. 31, 2006: Related U.S. Appl. No. 10/703,070—(Abandoned).

Advisory Action, mailed Oct. 20, 2006: Related U.S. Appl. No. 10/703,070—(Abandoned).

NonFinal Office Action, mailed Apr. 10, 2007: Related U.S. Appl. No. 10/703,070—(Abandoned).

Final Office Action, mailed Jun. 26, 2008: Related U.S. Appl. No. 10/703,070—(Abandoned).

Notice of Abandonment, mailed Jan. 23, 2009: Related U.S. Appl. No. 10/703,070—(Abandoned).

NonFinal Office Action, mailed Aug. 1, 2008: Related U.S. Appl. No. 11/129,540—(Abandoned).

NonFinal Office Action, mailed Apr. 28, 2009: Related U.S. Appl. No. 11/129,540—(Abandoned).

Final Office Action, mailed Nov. 27, 2009: Related U.S. Appl. No. 11/129,540—(Abandoned).

Notice of Abandonment, mailed Jun. 11, 2010: Related U.S. Appl. No. 11/129,540—(Abandoned).

Raúl Chirife et al., "Automatic Beat-To-Beat Left Heart AV Normalization: Is it Possible?", PACE, Nov. 2003; vol. 26, pp. 2103-2110.

R. Chirife et al., "Nonphysiological Left Heart AV Intervals as a Result of DDD and AAI "Physiological" Pacing", PACE, Nov. 1991; vol. 14, Part II, pp. 1752-1756.

Raul Chirife, "Proposal of a Method for Automatic Optimization of Left Heart Atrioventricular Interval Applicable to DDD Pacemakers", PACE, Jan. 1995; vol. 18, Part 1, pp. 49-56.

Raul Chirife, M.D., Letters to the Editor, PACE, May 2000; vol. 23, pp. 926.

Erich Ebner et al., "Ventricular Evoked Response as Clinical Marker for Hemodynamic Changes in Dilative Cardiomyopathy," PACE, Feb. 2004; vol. 27, pp. 166-174.

Toshiyuki Ishikawa et al., "Prediction of Optimal Atrioventricular Delay in Patients with Implanted DDD Pacemakers", PACE, Sep. 1999; vol. 22, pp. 1365-1371.

Ismer, B. et al, "Impact of Discriminating Electrophysiological and Electromechanical Determinants of the Optimal AV Delay in Right and Biventricular DDD Pacing," Folia Cardiol. 2006, tom 13, supl. C.

G. Schreier et al., "Correlation Between Changes in Stroke Volume and the Paced Intracardiac Electrogram," Europace, Jul. 2002; vol. 4, pp. 303-310.

Andreas Schuchert et al., "Effects of Body Position and Exercise on Evoked Response Signal for Automatic Threshold Activation," PACE, Oct. 1999; vol. 22, pp. 1476-1480.

Levine, Paul A. MD, FACC "Role of the AV Interval in DDD Pacing: Insights into Programming".

Levine, Paul A. MD, FACC, "Clinical Distribution, Ventricular Activation Sequence and Hemodynamics-3".

de Teresa, E. et al., "An Even More Physiological Pacing: Changing the Sequence of Ventricular Activation".

Levine, Paul A. MD, FACC, "Optimizing AV Delay in CRT Systems at Implant based on IACT".

NonFinal Office Action, mailed Nov. 17, 2005: Related U.S. Appl. No. 10/703,070—(Abandoned).

* cited by examiner

EXEMPLARY PR RHYTHMS
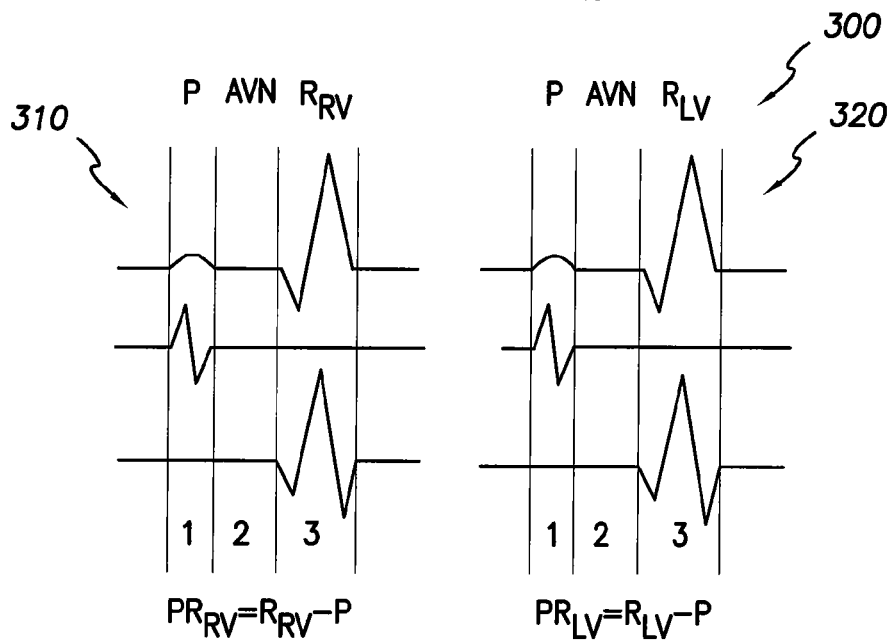
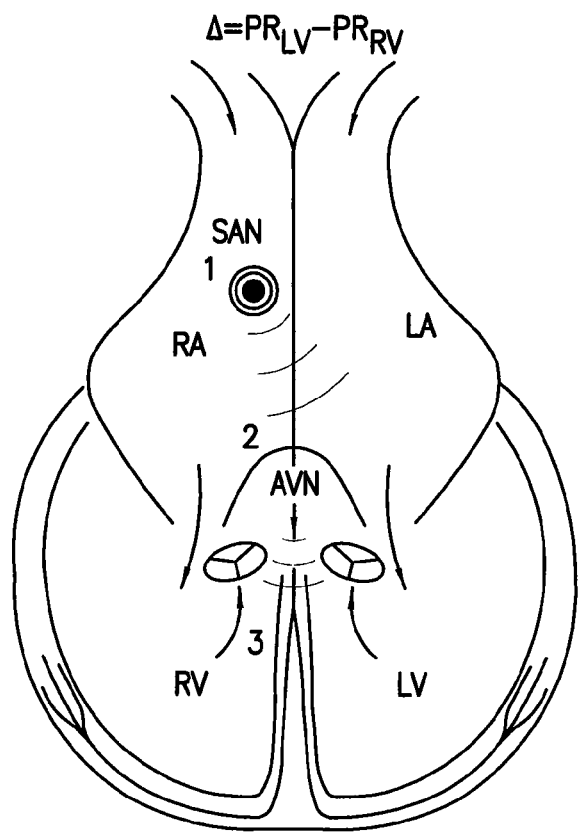
FIG. 3

EXEMPLARY AR RHYTHMS
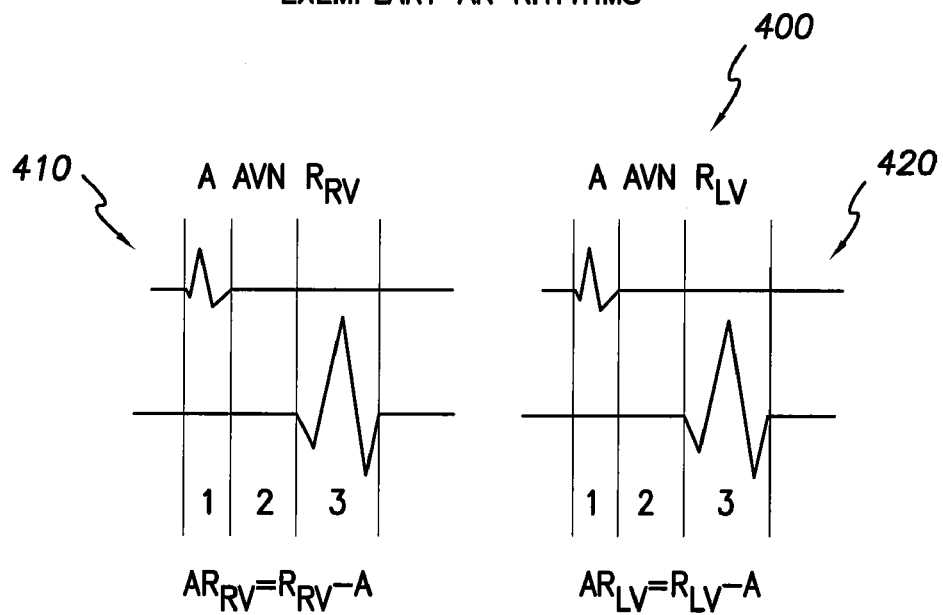
$AR_{RV} = R_{RV} - A$  $AR_{LV} = R_{LV} - A$
$\Delta = AR_{LV} - AR_{RV}$
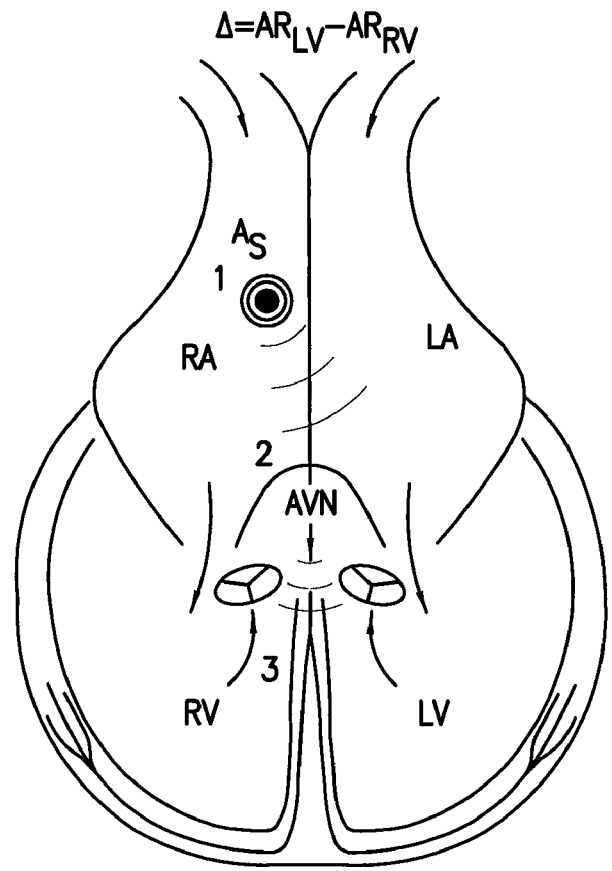
FIG. 4

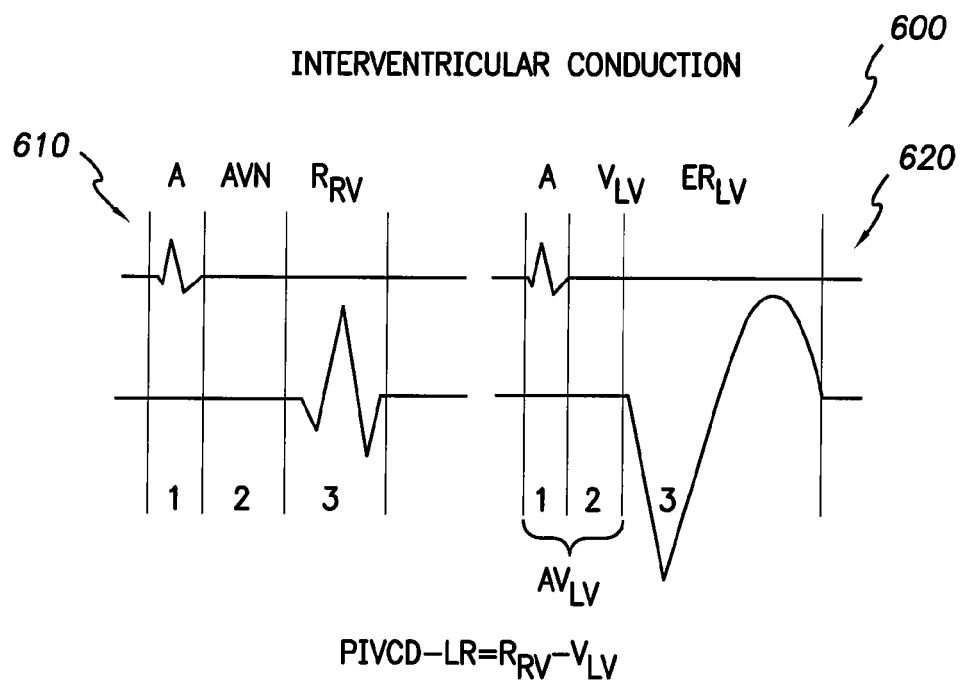
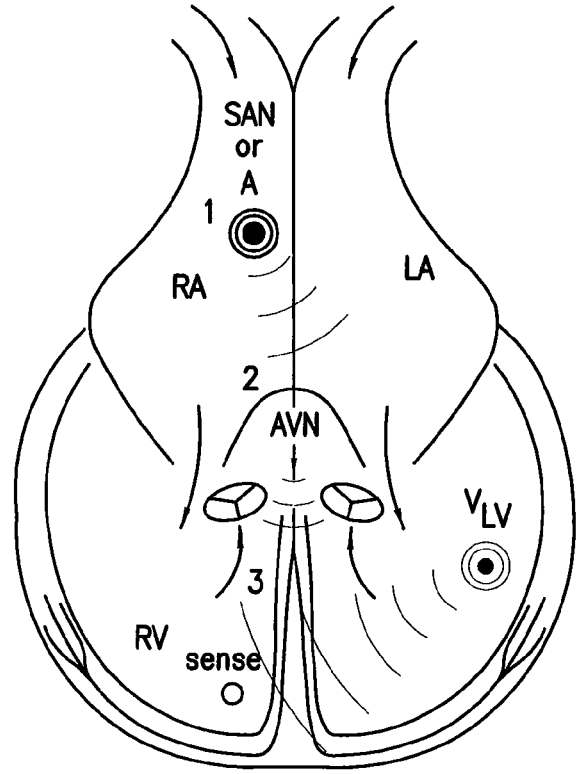
FIG. 6

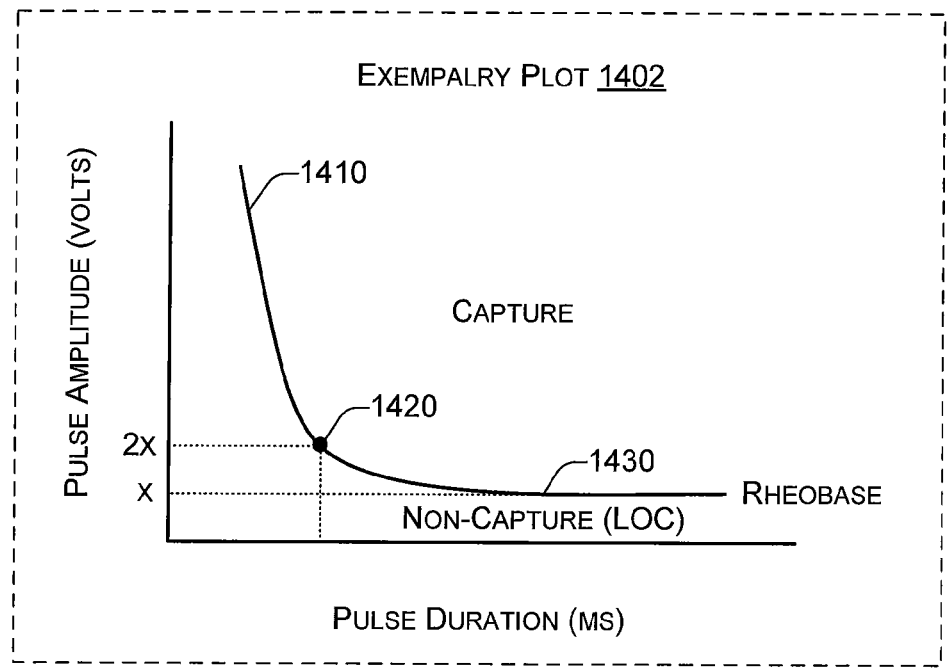
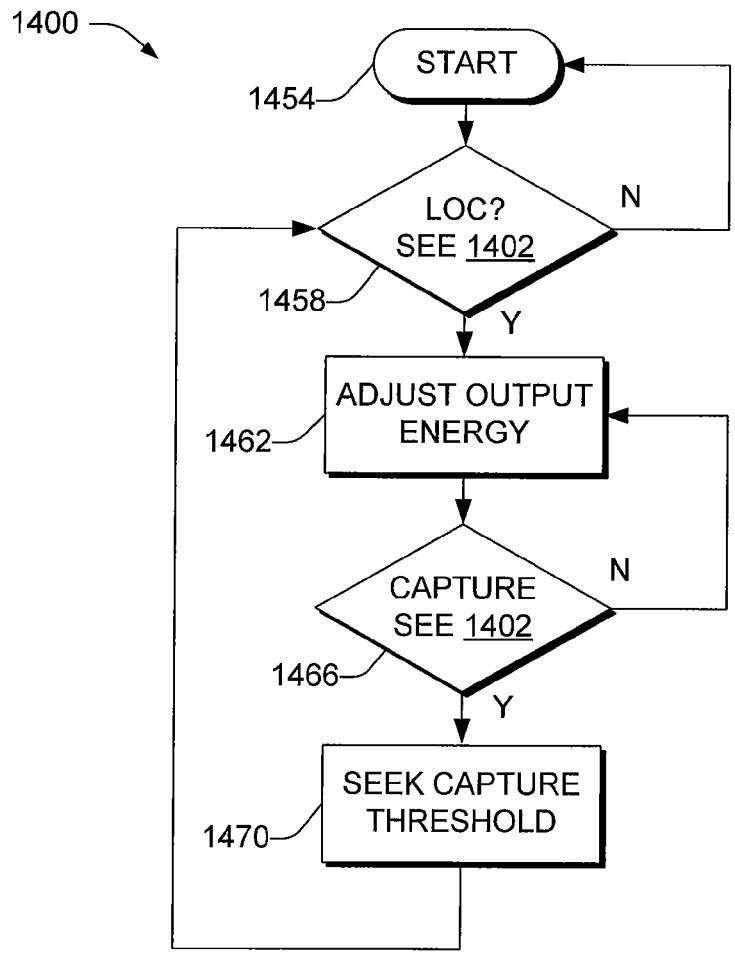
FIG. 14

US 7,881,787 B1

CAPTURE DETECTION SYSTEM AND METHOD CRT THERAPY

CROSS-REFERENCE TO RELATED APPLICATIONS

This application is related to U.S. patent application Ser. No. 11/129,540, filed May 13, 2005, titled "System and Method for Improving CRT Response and Identifying Potential Non-Responders to CRT Therapy", now abandoned, which claims the benefit of U.S. Provisional Application Ser. No. 60/664,763, filed Mar. 23, 2005 and which is a continuation-in-part of U.S. patent application Ser. No. 10/703,070, filed Nov. 5, 2003, titled "Methods for Ventricular Pacing", now abandoned. The aforementioned patent applications are incorporated by reference herein.

TECHNICAL FIELD

Subject matter presented herein pertains generally to cardiac pacing and/or stimulation therapy. More specifically, various exemplary technologies pertain to capture detection, especially where bi-ventricular pacing may be used.

BACKGROUND

Heart failure affects millions of people worldwide. Heart failure often manifests itself in relatively wide QRS signals, signifying a desynchronization between electrical activation of the right and left ventricles. Often, a left bundle branch block (LBBB) interrupts the normal conduction path to the left ventricle and results in the intrinsic conduction taking a relatively long time to reach the left ventricle, causing it to be activated well after the right ventricle. This dissynchrony results in a very inefficient contraction, resulting in very low cardiac output and patients who are unable to be very active. Over time, heart failure will progressively worsen and lead to death.

While some drug therapies may help some patients, electrical stimulation is more beneficial for those patients, assuming they meet certain criteria. Such stimulation is referred to as cardiac resynchronization therapy (CRT), which typically involves delivering electrical stimulation to the left ventricle prior to intrinsic conduction reaching the left ventricle, which results in a more synchronized contraction of the ventricles. CRT may include bi-ventricular therapy where electrical energy is delivered to both the right and the left ventricle. While delivery of energy to the right and left ventricles may occur simultaneously, in general, a delay exists, which is often referred to as an interventricular delay or interventricular pacing delay (VV delay).

For patients who meet the current CRT implant criteria, a relatively large percentage (about 30%) of those patients do not respond to CRT. Various reasons exist for a patient's failure to respond to CRT. For example, a patient's failure to respond may be due to cardiac condition or due to factors dictated by implementation of CRT. In particular, a lack of adequate capture assessment for bi-ventricular pacing is one reason a patient may fail to respond to CRT. Fusion between an intrinsic wavefront and an evoked response or between evoked responses can complicate capture assessment. If fusion is caused by VV timing, changing the VV delay may delivery non-optimal CRT and may even post some clinical risks. Further, if an RV pacing site and an LV pacing site are too close to each other, detection of an evoked response or evoked responses may be difficult. Consequently, a capture detection algorithm may fail to distinguish capture from non-capture or inadvertently label capture as loss of capture. In turn, such a failure may cause an implantable device to perform unnecessary actions or to adjust one or more therapy parameters in a non-optimal manner.

As discussed herein, various exemplary techniques aim to improve delivery of CRT by enabling or disabling a capture detection algorithm and/or by determining one or more CRT parameters that allow for adequate capture assessment. Other exemplary techniques are also discussed.

SUMMARY

An exemplary method includes implementing a cardiac pacing therapy capable of delivering bi-ventricular stimulation, deciding if the therapy calls for bi-ventricular stimulation and, if the therapy calls for bi-ventricular stimulation, comparing an interventricular conduction delay to a threshold and based on the comparing, deciding whether to enable a capture detection algorithm. Various other exemplary methods, devices, systems, etc. are also disclosed.

BRIEF DESCRIPTION OF THE DRAWINGS

Features and advantages of the described implementations can be more readily understood by reference to the following description taken in conjunction with the accompanying drawings.

FIG. 3 is an approximate anatomical diagram of a heart, a surface ECG and two IEGM waveforms that exhibit an intrinsic P wave and an R wave.

FIG. 4 is an approximate anatomical diagram of a heart and two IEGM waveforms that exhibit an A wave and an R wave.

FIG. 6 is an approximate anatomical diagram of a heart and two sets of IEGM waveforms wherein one set includes an evoked response in a left ventricle and the other set includes a response from a conducted event in a right ventricle.

FIG. 14 is a flow chart of a method that uses a capture detection or verification algorithm and a capture threshold search and an associated plot of capture and non-capture space.

DETAILED DESCRIPTION

The following description includes the best mode presently contemplated for practicing the described implementations. This description is not to be taken in a limiting sense, but rather is made merely for the purpose of describing the general principles of the implementations. The scope of the invention should be ascertained with reference to the issued claims. In the description that follows, like numerals or reference designators are used at times to reference like parts or elements throughout the description.

Overview

Exemplary methods, devices, systems, etc., pertain generally to pacing therapies and whether a therapy may reliably use beat-to-beat capture detection. For example, if a sensing electrode for the right ventricle and a sensing electrode for the left ventricle are physically and/or "electrically" close to each other, then sensed activity may not allow a capture detection algorithm to reliably distinguish capture from fusion. Also consider a situation where a sensing electrode is positioned between two foci and where stimuli are delivered within a certain time interval from the two foci. In this situation, the sensing electrode may sense a fused waveform, which may confound capture detection. Where such circumstances exist, an exemplary method may disable beat-to-beat capture detection and optionally call for techniques that allow for reliable capture detection where pacing to one ventricle is temporarily disabled. Of course, circumstances may change over time, hence, various exemplary techniques may uncover a change and respond accordingly (e.g., enable capture detection, select a different electrode configuration, adjust one or more pacing parameters, etc.).

The following description begins with a discussion of exemplary implantable devices and associated components followed by a discussion of heart rhythms and associated waveforms. Next, a discussion of cardiac performance follows, and the detailed description continues with a discussion of various exemplary methods, devices, systems, etc.

Exemplary Stimulation Device

The techniques described below are intended to be implemented in connection with any stimulation device that is configured or configurable to stimulate nerves and/or stimulate and/or shock a patient's heart.

Figure 1:
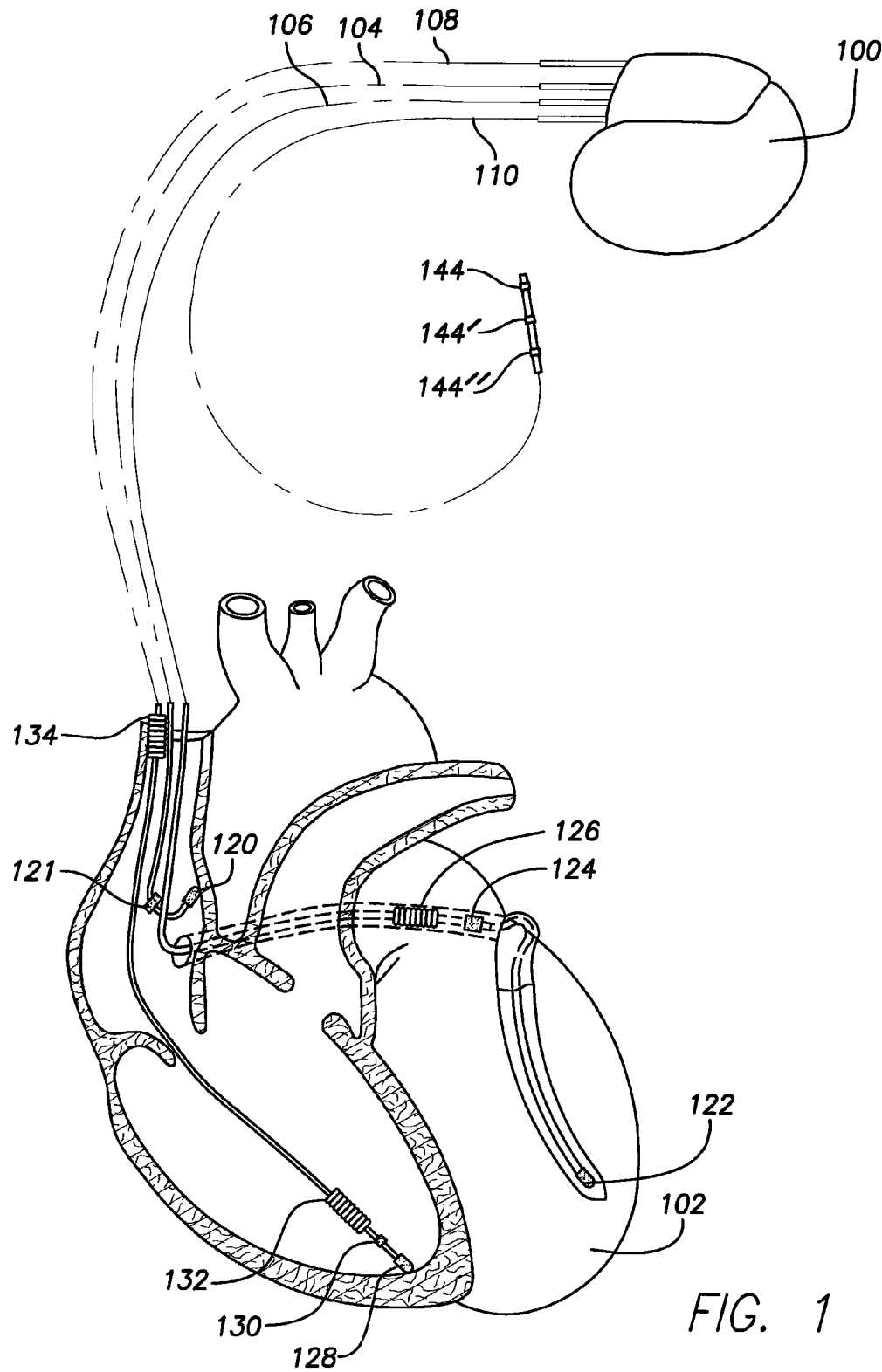
FIG. 1 is a simplified diagram illustrating an exemplary implantable stimulation device in electrical communication with at least three leads implanted into a patient's heart and at least one other lead for delivering stimulation and/or shock therapy. Other devices with fewer leads may also be suitable in some circumstances.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of autonomic nerves. In addition, the device 100 may optionally include a fourth lead 110 having, in this implementation, three electrodes 144, 144', 144" suitable for stimulation of autonomic nerves. This lead may be positioned in and/or near a patient's heart or near an autonomic nerve within a patient's body and remote from the heart. Of course, such a lead may be positioned epicardially or at some other location to stimulate other tissue.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation of autonomic nerves.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein. As will be described in greater detail below, the illustrative method tests one or more placement locations of the coronary sinus lead 106 to determine a suitable placement for lead 106.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves. Such a lead may include pacing and autonomic nerve stimulation functionality and may further include bifurcations or legs. For example, an exemplary coronary sinus lead includes pacing electrodes capable of delivering pacing pulses to a patient's left ventricle and at least one electrode capable of stimulating an autonomic nerve. An exemplary coronary sinus lead (or left ventricular lead or left atrial lead) may also include at least one electrode capable of stimulating an autonomic nerve, such an electrode may be positioned on the lead or a bifurcation or leg of the lead.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating an autonomic nerve, such an electrode may be positioned on the lead or a bifurcation or leg of the lead.

Figure 2:
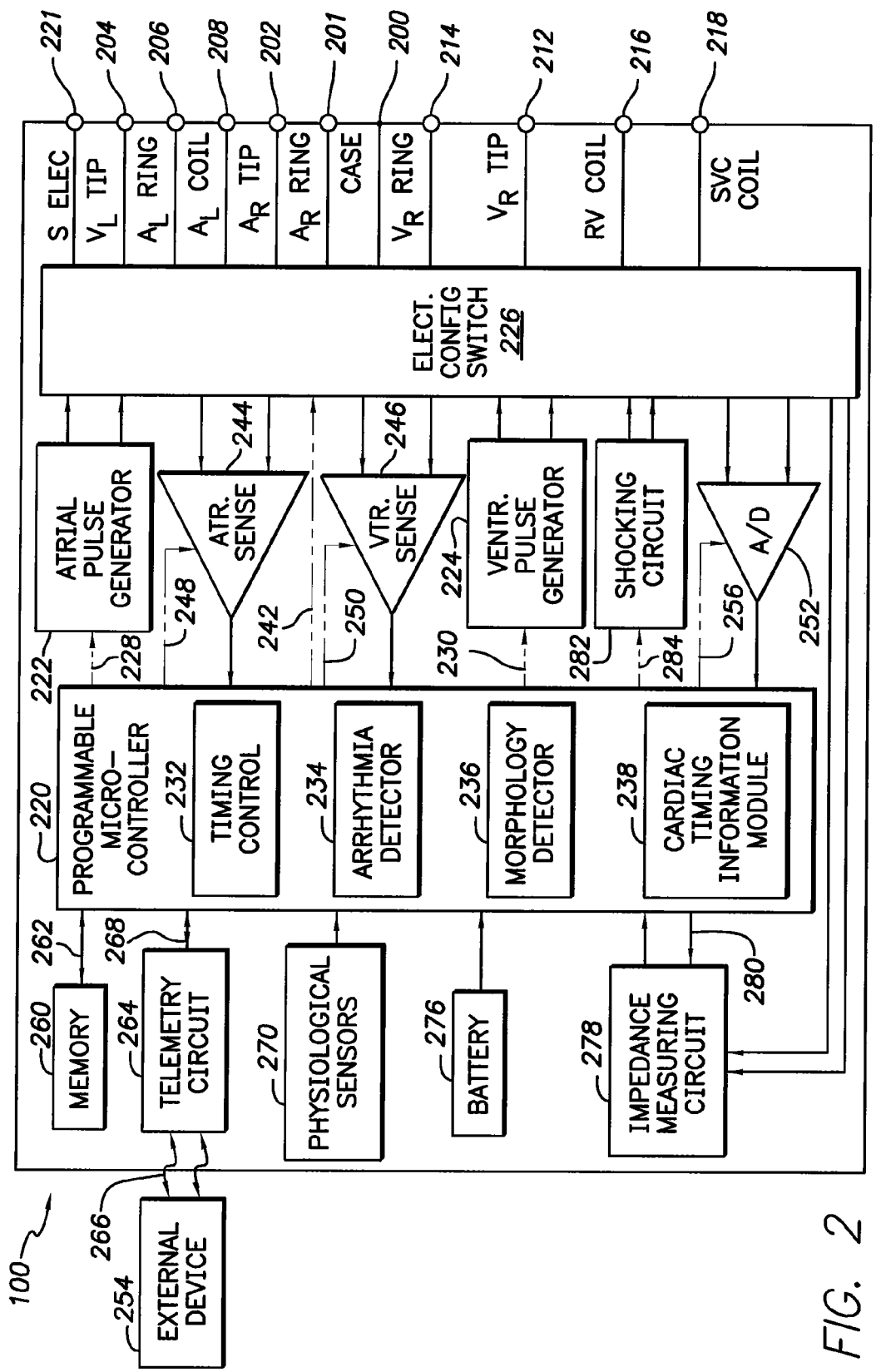
FIG. 2 is a functional block diagram of an exemplary implantable stimulation device illustrating basic elements that are configured to provide cardioversion, defibrillation, pacing stimulation and/or other tissue and/or nerve stimulation. The implantable stimulation device is further configured to sense information and administer stimulation pulses responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. The stimulation device can be solely or further capable of delivering stimuli to autonomic nerves. While a particular multi-chamber device is shown, it is to be appreciated and understood that this is done for illustration purposes only. For example, various methods may be implemented on a pacing device suited for single ventricular stimulation and not bi-ventricular stimulation. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart with cardioversion, defibrillation, pacing stimulation, and/or autonomic nerve stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or autonomic stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable autonomic nerve stimulation electrodes is also possible via these and/or other terminals (e.g., via a nerve stimulation terminal S ELEC 221).

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively. Connection to suitable autonomic nerve stimulation electrodes is also possible via these and/or other terminals (e.g., via the nerve stimulation terminal S ELEC 221).

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander et al.) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves or other tissue) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (AA) delay, or ventricular interconduction (VV) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

Microcontroller 220 further includes a cardiac timing information module 238 for determining a selected cardiac timing parameter. As described above, in one embodiment module 238 determines an intrinsic conduction delay between right ventricular activation and left ventricular activation. In other embodiments, module 238 determines an interval between stimulation of one ventricle and sensing of propagated electrical activity to the other ventricle. Module 238 may be implemented in hardware as part of the microcontroller 220, or as software/firmware instructions programmed into the device and executed on the microcontroller 220 during certain modes of operation. The module 238 may be used with various exemplary techniques described further below.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. In some instances, detection or detecting includes sensing and in some instances sensing of a particular signal alone is sufficient for detection (e.g., presence/absence, etc.).

The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes. The microcontroller 220 may control the A/D system 252 via a control line 256, for example, to select a resolution, a gain, a ground, etc., which may occur in conjunction with one or more other instructions (e.g., an instruction to the switch 226, etc.).

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AA delay, AV delay, VV delay, etc.) at which the atrial and ventricular pulse generators, 222 and 224, generate stimulation pulses.

While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, hemodynamics, pressure, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et al.), issued Dec. 19, 1995, which patent is hereby incorporated by reference.

More specifically, the physiological sensors 270 optionally include sensors for detecting movement and minute ventilation in the patient. The physiological sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 □A), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to approximately 0.5 J), moderate (e.g., approximately 0.5 J to approximately 10 J), or high energy (e.g., approximately 11 J to approximately 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode). Other exemplary devices may include one or more other coil electrodes or suitable shock electrodes (e.g., a LV coil, etc.).

Cardioversion level shocks are generally considered to be of low to moderate energy level (where possible, so as to minimize pain felt by the patient), and/or synchronized with an R-wave and/or pertaining to the treatment of tachycardia. Defibrillation shocks are generally of moderate to high energy level (i.e., corresponding to thresholds in the range of approximately 5 J to approximately 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

As described below, an exemplary implantable device may include a power source (e.g., a battery or other power source), a processor (e.g., microprocessor 220), memory (e.g., memory 260) and control logic to perform any of a variety of actions. For example, control logic may call for acquisition of a paced or a sensed interventricular conduction delay (e.g., IVCD) and may enable or disable a beat-to-beat capture detection algorithm (e.g., for use in a bi-ventricular pacing therapy) based on a comparison of an acquired paced or a sensed interventricular conduction delay to a threshold. Other exemplary actions are possible (see, e.g., methods 1600, 1700, 1800, 1900, 2000, 2100). Control logic may be in the form of instructions on a computer-readable medium (e.g., memory 260 of FIG. 2) where the instructions are executable by a processor (e.g., the microprocessor 220 of FIG. 2).

Heart Rhythms

FIG. 3 shows an approximate anatomical diagram of a heart and two sets of PR waveforms 300. One set of waveforms 310 corresponds in part to right ventricular activity while another set of waveforms 320 corresponds in part to left ventricular activity. Action potentials propagating through a normal heart are labeled as follows: 1, associated with the sinoatrial node (SAN) and the atria; 2, associated with the atrio-ventricular node (AVN); and 3, associated with right and left bundle branches of the ventricles. In a normal heart, cells of the SAN (1) spontaneously depolarize and thereby initiate an action potential (shown as dashed lines emanating from the SAN). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

FIG. 3 also shows two surface electrocardiograms (ECG) of normal heart activity (e.g., polarization, depolarization, etc.) wherein atrial depolarization is represented as a "P wave" and ventricular depolarization is represented as an "R wave", or QRS complex. The right ECG shows a P wave followed by an AVN conduction delay (AVN) and a right ventricular R wave or QRS complex ($R_{RV}$). The left ECG shows a P wave followed by an AVN conduction delay (AVN) and a left ventricular R wave or QRS complex ($R_{LV}$). In this example, the right and left ventricular R waves ($R_{RV}$ and $R_{LV}$) are due to conduction through the atrio-ventricular node and not due to artificially paced events. The sets of plots 310, 320 include approximate atrial IEGM waveforms and approximate ventricular IEGM waveforms, for example, as sensed by an atrial sensing channel and one or more ventricular sensing channels.

Often detection of an R wave or QRS complex in an IEGM relies on signal amplitude or signal derivative with respect to time. Further, many detection methods are capable of assigning a time to a detected R wave or QRS complex or assigning a time span to a P wave to R wave or QRS complex interval, which are shown in FIG. 3 as $PR_{RV}$ for the right ventricle and $PR_{LV}$ for the left ventricle. If $PR_{RV}$ and $PR_{LV}$ are approximately equal, then the right ventricle and the left ventricle contract in a synchronous manner. For example, in a normal heart, the delay between contraction of the right ventricle and the left ventricle may be around 5 ms. However, if $PR_{RV}$ and $PR_{LV}$ differ substantially, e.g., $|\Delta|=|PR_{LV}-PR_{RV}|>5$ ms, then the right ventricle and left ventricle contract in an asynchronous manner, which may indicate some degree of cardiac dysfunction.) The embodiments described herein use the $\Delta$ value to determine whether the current lead positioning is adequate, or whether it needs to be changed.

The variable $\Delta$ represents an interventricular delay that is based on an atrio-ventricular delay for the left ventricle ($PR_{LV}$) and an atrio-ventricular delay for the right ventricle ($PR_{RV}$). The variable $|\Delta|$ is shown as the absolute value of the difference while herein and in the figures the variable $\Delta$ (e.g., $\Delta = PR_{LV}-PR_{RV}$) may be less than zero when $PR_{RV}$ exceeds $PR_{LV}$ or greater than zero when $PR_{LV}$ exceeds $PR_{RV}$. Described further below is a variable referred to as a paced interventricular conduction delay ($\Delta_{PIVCD}$), which relies on pacing in one ventricle and sensing in the other ventricle and optionally vice versa. In general, the acronym IVCD (e.g., IVCD, IVCD-RL, IVCD-LR or $\Delta_{IVCD}$) may refer to one or more types of interventricular conduction delays, whether paced ventricular, paced atrial, or intrinsic. An interventricular conduction delay, regardless of type, pertains to direction of a wavefront, i.e., from left ventricle to right ventricle or from right ventricle to left ventricle. An IVCD generally depends on a position of an electrode and/or electrode configuration.

With respect to cardiac condition, a long interventricular delay may be indicative of a conduction block. For example, left bundle branch block (LBBB) may cause the left ventricle to contract more than approximately 50 ms after contraction of the right ventricle (e.g., $\Delta>0$). Whereas a right bundle branch block (RBBB) may be expected to cause the right ventricle to contract well after the left ventricle (e.g., $\Delta<0$). Of course, a patient may have RBBB and LBBB of similar extent such that interventricular delay does not indicate whether a block could be RBBB or LBBB. In such circumstances, atrio-ventricular delay may indicate block. For example, an atrio-ventricular delay of more than approximately 200 ms in a non-atrial paced heart may indicate some degree of block or conduction problem while an atrio-ventricular delay of more than approximately 250 ms in an atrial paced heart may indicate some degree of block or conduction problem.

FIG. 4 shows an approximate anatomical diagram of a heart and two sets of waveforms 400. One set of waveforms 410 corresponds in part to right ventricular activity while another set of waveforms 420 corresponds in part to left ventricular activity. Action potentials propagating through the heart are labeled as follows: 1, associated with a paced atrial stimulus and the atria; 2, associated with the atrio-ventricular node (AVN); and 3, associated with right and left bundle branches of the ventricles. In an atrial paced heart, cells depolarize near a pacing site (1) and thereby initiate an action potential (shown as dashed lines emanating from the pacing site). This action potential propagates rapidly through the atria (which contract), slowly through the AVN (2) and then to the ventricles (3), which causes contraction of the right and left ventricles. Thus, in a normal heart, ventricular rhythm relies on conduction of action potentials through the AVN and through the left and right bundle branches.

The two sets of waveforms 410, 420 show various IEGMs of heart activity (e.g., polarization, depolarization, etc.) wherein atrial depolarization is represented as an "A wave" and ventricular depolarization is represented as an "R wave", or QRS complex. Both sets 410, 420 show an A wave followed by an AVN conduction delay (AVN) and a right ventricular R wave or QRS complex ($R_{RV}$) for the set 410 and a left ventricular R wave or QRS complex ($R_N$) for the set 420. Often detection of an R wave or QRS complex relies on signal amplitude or signal derivative with respect to time. Further, many detection methods are capable of assigning a time to a detected R wave or QRS complex or assigning a time span to an A wave to R wave or QRS complex interval, which are shown in FIG. 4 as $AR_{RV}$ for the right ventricle and $AR_{LV}$ for the left ventricle. If $AR_{RV}$ and $AR_{LV}$ are approximately equal, then the right ventricle and the left ventricle contract in an approximately synchronous manner. However, if $AR_{RV}$ and $AR_{LV}$ differ substantially, e.g., $|\Delta|=|AR_{LV}-AR_{RV}|>5$ ms, then the right ventricle and left ventricle contract in an asynchronous manner. Depending on patient or other factors, the time could be set at some time other than 5 ms. The variable $|\Delta|$ is shown as the absolute value of the difference while herein and in the figures the variable $\Delta$ (e.g, $\Delta = AR_{LV}-AR_{RV}$) may be less than zero when $AR_{RV}$ exceeds $AR_{LV}$ or greater than zero when $AR_{LV}$ exceeds $AR_{RV}$.

To facilitate measurement of $AR_{RV}$ or $AR_{LV}$, in instances where ventricular pacing occurs, the AV delay (e.g., $AV_{RV}$ and/or $AV_{LV}$) may be increased to a value greater than the expected $AR_{RV}$ or $AR_{LV}$. Of course, where possible, ventricular pacing is optionally disabled, set to a back-up mode, etc.

Figure 5:
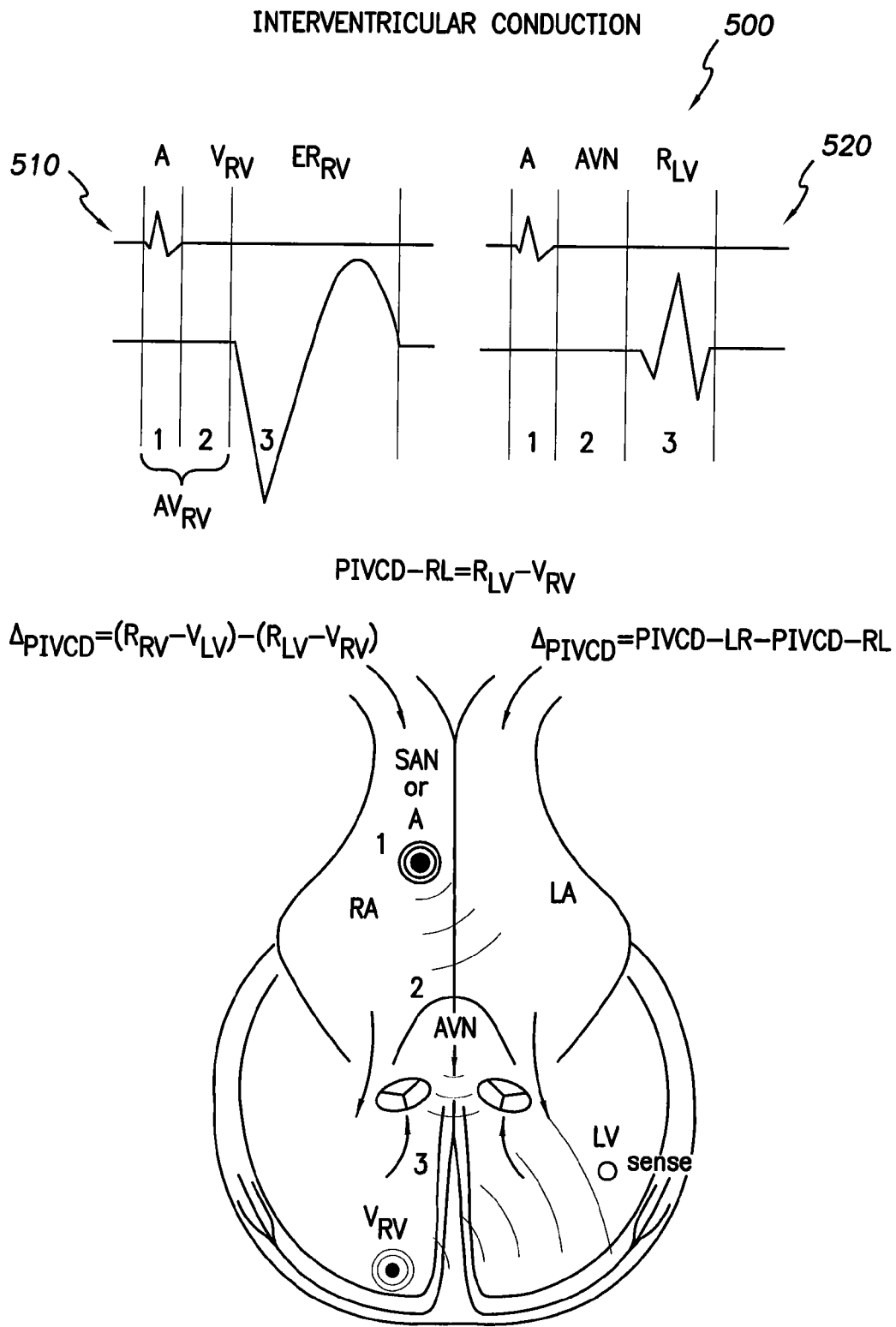
FIG. 5 is an approximate anatomical diagram of a heart and two sets of IEGM waveforms wherein one set includes an evoked response in a right ventricle and the other set includes a response from a conducted event in a left ventricle.

FIGS. 5 and 6 show plots, approximate anatomical diagrams and equations associated with yet another delay time, $\Delta_{PIVCD}$, referred to a paced interventricular conduction delay (PIVCD) or, more generally an interventricular conduction delay (IVCD or $\Delta_{IVCD}$). FIG. 5 pertains to pacing in a right ventricle and sensing in a left ventricle wherein the time between pacing and sensing is referred to as a right to left PIVCD or PIVCD-RL, which equals $R_{LV}$–$V_{RV}$, wherein $V_{RV}$ is a pace time of a pacing stimulus in the right ventricle and $R_{LV}$ is a sense time of an evoked response wavefront in the left ventricle due to the paced stimulus in the right ventricle. Thus, PIVCD-RL is normally greater than zero. To ensure that the pacing stimulus in the right ventricle results in an evoked response, a capture routine or algorithm may be implemented. Thus, various exemplary methods, devices and/or systems include a capture algorithm (e.g., autocapture). Various exemplary methods related to capture are discussed further below.

FIG. 5 shows a set of waveforms 510 that include an atrial event (e.g., A or P), an atrial to ventricular paced delay $AV_{RV}$, a ventricular pace time $V_{RV}$ and a sensed evoked response in the right ventricle $ER_{RV}$. Another set of waveforms 520 pertains primarily to the left ventricle and includes an atrial event (e.g., A or P), an AVN delay and a sensed evoked response in the left ventricle $R_{LV}$ which is a result of the stimulus $V_{RV}$ in the right ventricle. To ensure that the sensed evoked response in the left ventricle $R_{LV}$ is not due to conducted electrical activity from the atria, a sufficiently short ventricular paced delay $AV_{RV}$ is used. For example, a paced delay $AV_{RV}$ of approximately 30 ms to approximately 70 ms may suffice. In one example, $AV_{RV}$ is set to approximately 50 ms to approximately 80 ms. $AV_{RV}$ may also be set sufficiently short to avoid fusion. While AV is referred to, PV may also apply where appropriate.

In general, bipolar sensing (or other multipolar/combipolar sensing) may increase signal to noise of the sensed activation in the left ventricle when compared to unipolar sensing that includes use of an in vivo, yet non-local electrode such as a pulse generator can. The latter technique is more often used in detection of evoked response or applications utilizing far-field signals. Further, bipolar sensing that includes two electrodes positioned in proximity to each other (e.g., less than approximately 4 cm), may increase signal to noise and sensitivity and better sense timing of an activation wave front proximate to the electrodes.

FIG. 6 pertains to pacing in a left ventricle and sensing in a right ventricle wherein the time between pacing and sensing is referred to as a left to right PIVCD or PIVCD-LR, which equals $R_{RV}$–$V_{LV}$, wherein $V_{LV}$ is a pace time of a pacing stimulus in the left ventricle and $R_{RV}$ is a sense time of a left ventricle, evoked response wavefront in the right ventricle due to the paced stimulus in the left ventricle. Thus, PIVCD-LR is normally greater than zero. To ensure that the pacing stimulus in the left ventricle results in an evoked response, a capture routine or algorithm may be implemented. Thus, various exemplary methods, devices and/or systems include a capture algorithm (e.g., autocapture). Various exemplary methods related to capture are discussed further below.

FIG. 6 shows a set of waveforms 620 that includes an atrial event (e.g., A or P), an atrial to ventricular paced delay $AV_{LV}$, a ventricular pace time $V_{LV}$ and a sensed evoked response in the left ventricle $ER_{LV}$. Another set of waveforms 610 pertains primarily to the right ventricle and includes an atrial event (e.g., A or P), an AVN delay and a sensed evoked response in the right ventricle $R_{RV}$ which is a result of the stimulus $V_{LV}$ in the left ventricle. To ensure that the sensed evoked response in the right ventricle $R_{RV}$ is not due to conducted electrical activity from the atria, a sufficiently short ventricular paced delay $AV_{LV}$ is used. For example, a paced delay $AV_{LV}$ of approximately 30 ms to approximately 70 ms may suffice. In one example, $AV_{LV}$ is set to approximately 50 ms to approximately 80 ms. $AV_{LV}$ may also be set sufficiently short to avoid fusion. While AV is referred to, PV may also apply where appropriate.

In general, bipolar sensing (or other multipolar/combipolar sensing) may increase signal to noise of the sensed activation response in the left ventricle when compared to unipolar sensing that includes use of an in vivo, yet non-local electrode such as a pulse generator can. The latter technique is often more used in detection of evoked response or the applications utilizing far-field signals. Further, bipolar sensing that includes two electrodes positioned in proximity to each other (e.g., less than approximately 4 cm), may increase signal to noise and sensitivity and better localize an activation wavefront.

Various exemplary methods described herein are optionally implemented using an implantable device having a single sensing channel for one or more electrodes positioned in or on the right ventricle and for one or more electrodes positioned in or on the left ventricle. In such devices, switching is optionally used to switch between sensing of the right ventricle and the left ventricle. Alternatively, both ventricles are sensed at the same time wherein an algorithm or other detection method is used to distinguish at least some information associated with the right ventricle from at least some information associated with the left ventricle.

Figure 7:
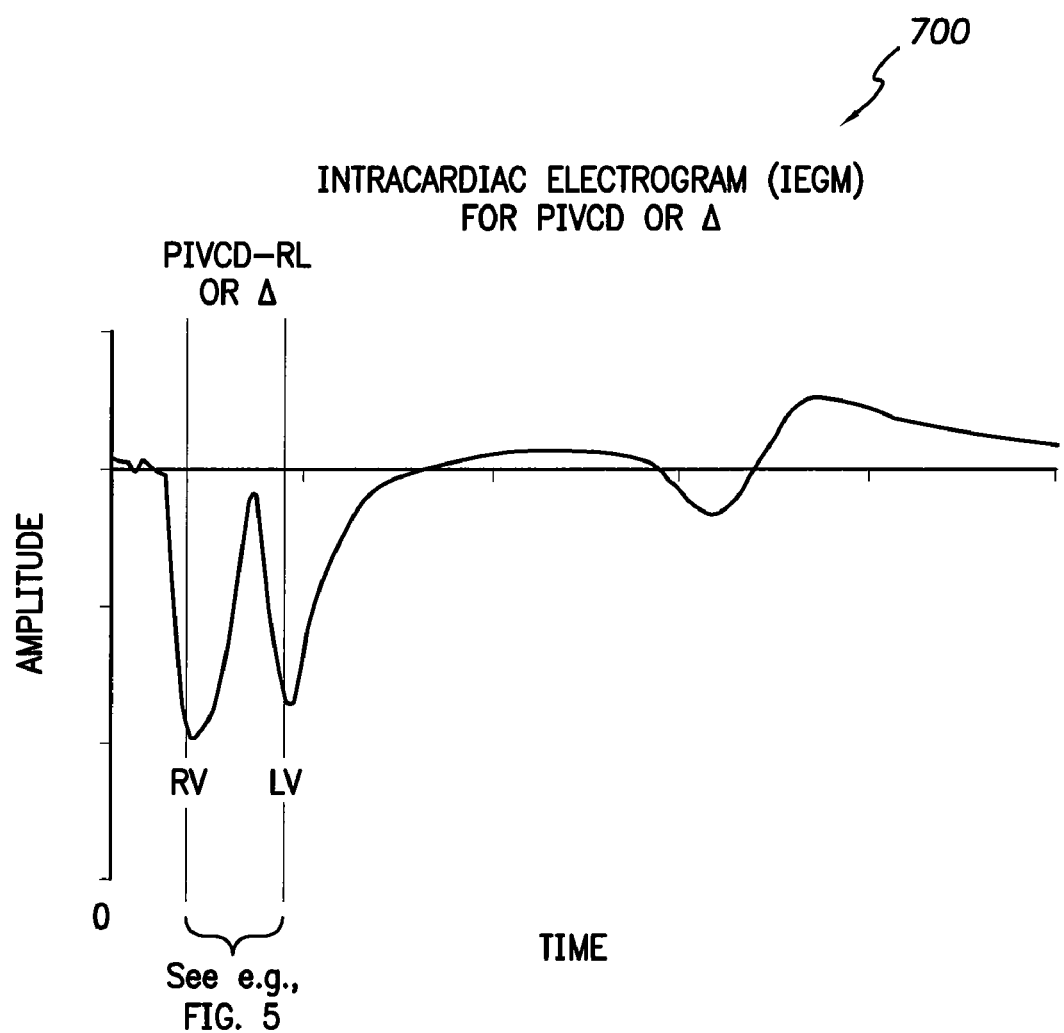
FIG. 7 is an exemplary IEGM plot acquired in a study using a unipolar sensing arrangement for a right ventricular tip electrode and a left ventricular tip electrode having a common electrode.

FIG. 7 shows an exemplary IEGM plot 700 acquired in a study using a unipolar sensing arrangement for a right ventricular tip electrode and a left ventricular tip electrode having a common electrode (e.g., can, device sensing circuit, etc.). In this unipolar arrangement, an electrical connection exists between right and left ventricular sensing circuits. In particular, depolarization due to atrio-ventricular intrinsic conduction was sensed at the right ventricle and then sensed at the left ventricle as the activation propagated to the left ventricle, and is identified by the two discernible peaks shown in FIG. 7 and corresponding to right ventricular activation and left ventricular activation, respectively. In this example, the peak-to-peak time delay typically approximates Δ and may be used to determine whether the lead positions are suitable. However, it may approximate PIVCD-RL in the case of FIGS. 5 and 6. If RV is paced at a short AV delay (such that no intrinsic conduction will have yet arrived at the ventricles), the time delay from pacing RV to the peak of the conduction to the left ventricle approximates PIVCD-RL. In an alternative example, not shown in FIG. 13, a pacing stimulus may be delivered to the right ventricle at a time of approximately 0 ms. This pacing stimulus will result in capture of the right ventricle and the IEGM will show a corresponding right ventricular evoked response. In this example, the left ventricle is not paced or initially captured by the pace to the right ventricle but after a short delay, the left ventricle will depolarize due to conduction of the paced event from the right ventricle. Hence, the delay between the right ventricular peak (RV) and the left ventricular peak (LV) approximates a paced interventricular conduction delay from right ventricle to left ventricle (see, e.g., PIVCD-RL of FIG. 5). Thus, the plot 700 helps to demonstrate a particular exemplary manner in which an implantable device that uses a single sensing amplifier for right and left ventricular sensing channels can determine paced interventricular conduction delay.

Further, some implantable devices having sensing and pacing capabilities can deliver a stimulus to one ventricle and then switch to sensing of both ventricles. For example, in the plot 700, the RV stimulus may have been delivered in an open configuration (e.g., RV and LV leads/electrodes not "connected") and, thereafter, leads/electrodes "shorted" to allow for sensing from both ventricles. Of course, where appropriate, pacing in one ventricle and sensing in the other ventricle may occur according to various arrangements.

Figure 8:
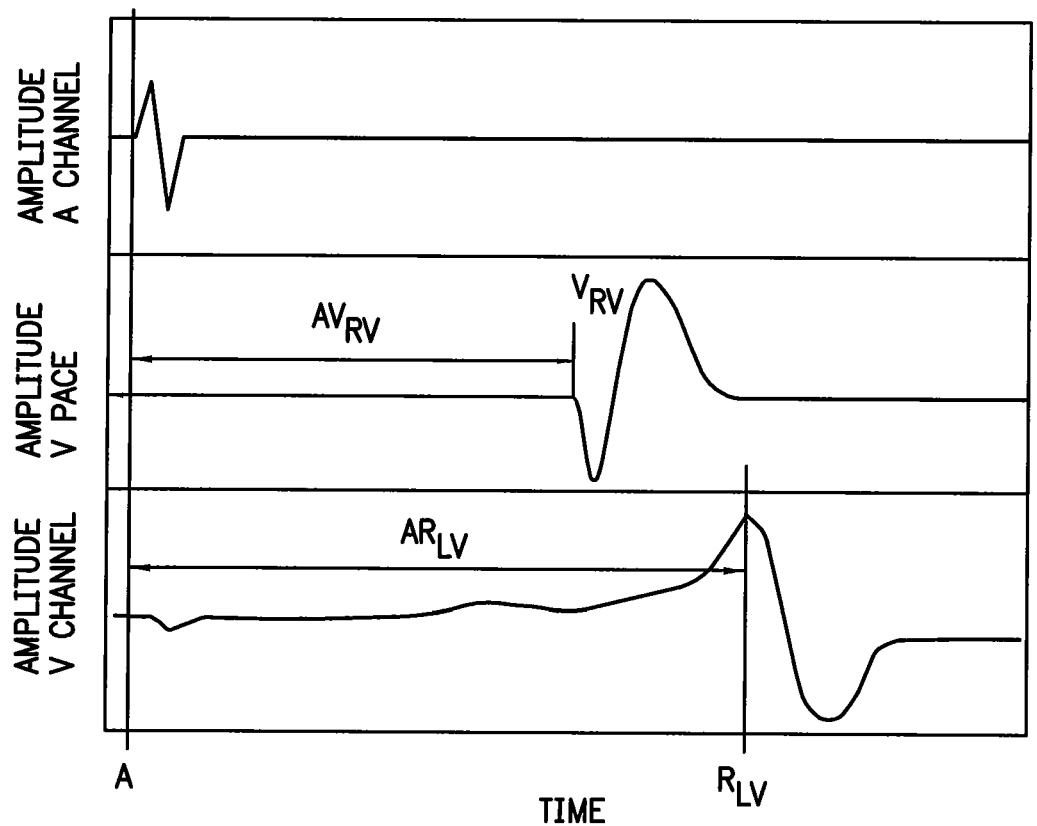
FIG. 8 is an exemplary atrial and ventricular IEGM plot acquired in a study using an implantable device optionally including a switchable channel for RV and LV sensing and/or pacing.

FIG. 8 shows an exemplary IEGM plot 800 wherein the ventricular IEGM was acquired using an implantable device including a switchable channel for RV and LV sensing. Such a device may allow for measurement of $AR_{RV}/PR_{RV}$ and $AR_{LV}/PR_{LV}$ by switching between RV sensing to LV sensing. Accordingly, Δ may be ascertained. Such a device may also allow for pacing in the right ventricle and/or left ventricle. Further, such a device may ascertain PIVCD-RL and/or PIVCD-LR. For example, if an $AV_{RV}$ or $PV_{RV}$ delay is set short enough to avoid fusion, then $AR_{LV}$ or $PR_{LV}$ may be determined on the basis of LV sensing wherein the LV sensing sense electrical activity in the left ventricle (e.g., $R_{LV}$) stemming from the right ventricular stimulus (e.g., $V_{RV}$). In this example, PIVCD-RL may equal $AR_{LV}-AV_{RV}$ or $PR_{LV}-PV_{RV}$. As already mentioned, an IVCD may stem from an atrial stimulus (paced or intrinsic) conducted to a ventricle (i.e., the "paced" ventricle of a PIVCD) which subsequently conducts to the other ventricle (i.e., the sensed ventricle of a PIVCD).

Other implantable devices may include RV and LV sensing channels that can operate at the same time. Such devices may allow for measurement of $AR_{RV}/PR_{RV}$ and $AR_{LV}/PR_{LV}$ on a beat-by-beat basis. For example, for a single beat, an atrial to right ventricular delay and an atrial to left ventricular delay may be ascertained. Such an exemplary method can reduce measurement error by determining such variable for a single beat as compared to determining one variable for one beat and another variable for a different beat. Detection of an event may be based on sensitivity programmed in devices or a criterion such as an amplitude value greater than approximately 40% of an expected QRS amplitude value.

Various exemplary methods, devices and/or systems may help to avoid cross ventricular sensing. For example, if an interventricular delay is less than interventricular conduction (e.g., PIVCD-RL and PIVCD-LR), the incidence of sensing paced ventricular events in an alert interval is reduced. Further, this incidence may be further reduced through use of an automatic capture algorithm.

Figure 9B:
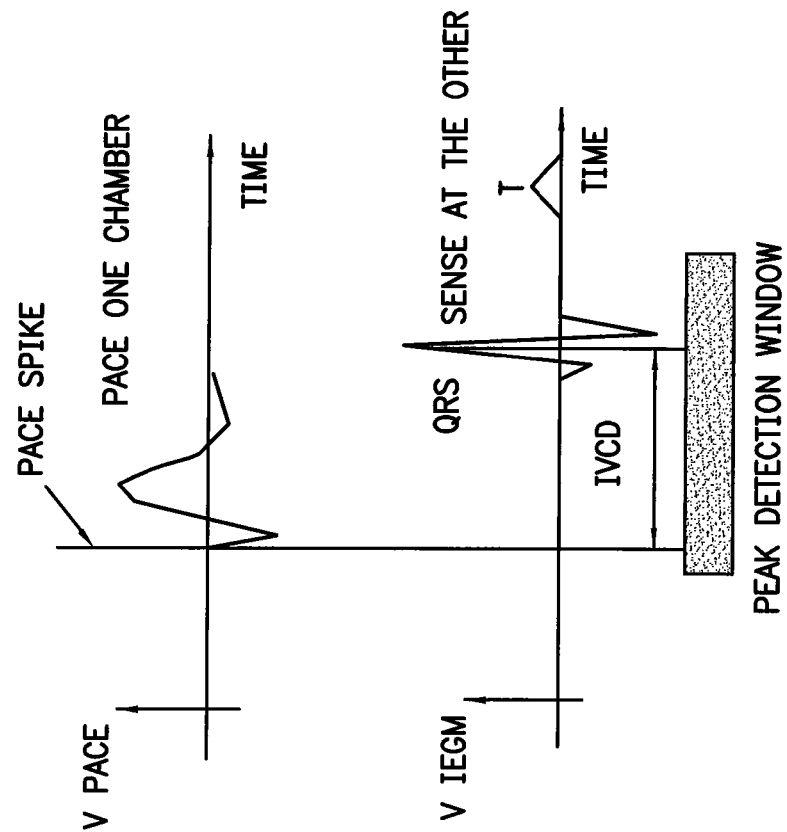
FIGS. 9A and 9B depict ventricular activity as sensed by independent sense channels and illustrate an embodiment in which the atrial activity is not required.
Figure 9A:
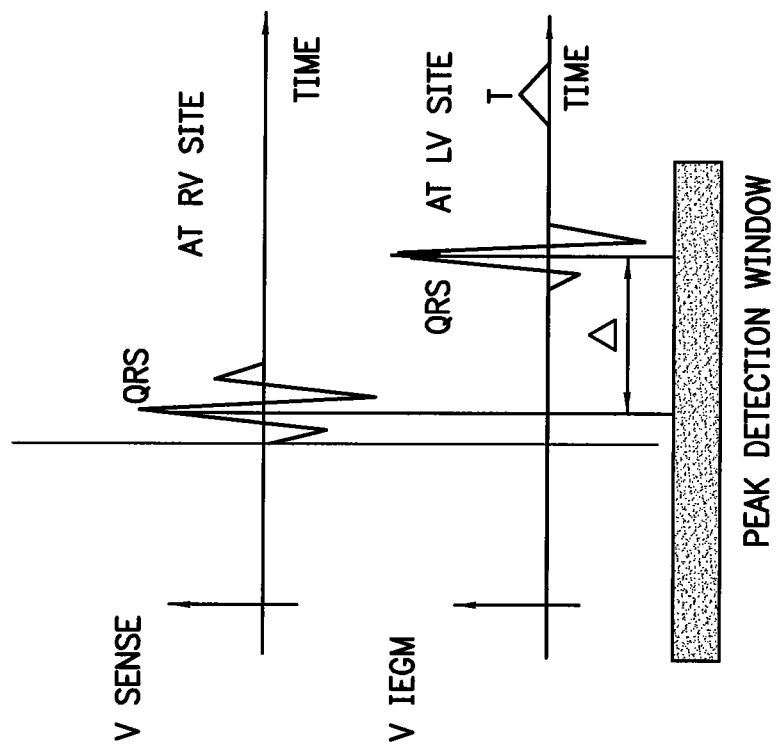

FIGS. 9A and 9B show exemplary IEGM plots 900 of ventricular activity as sensed by a pair of sensing channels, V SENSE and V IEGM. This ventricular activity may be used in one embodiment that does not rely on atrial activity to determine the IVCD or Δ; rather, by simply monitoring the right ventricular and left ventricular activity, the IVCD or Δ value can be determined. As shown in FIG. 9A, the Δ value can be determined by monitoring a first channel (the "V SENSE" channel) for right ventricular activity and a second channel (the "V IEGM" channel) for left ventricular activity. While many different ways of detecting activity can be employed, in this embodiment the peaks are used to detect activity, and the peak-to-peak interval is used to determine the Δ value. In addition, while the RV is shown as being the first ventricle to intrinsically activate, it will be understood that in some patients the LV may activate prior to the RV.

As shown in FIG. 9B, a ventricular pace spike in one chamber (e.g., the right ventricle) initiates the IVCD interval, and detection of the peak of the QRS on the V IEGM channel signifies the end of the IVCD interval. Alternatively, capture verification may be performed in the first chamber (e.g., to detect the peak of the evoked response), and the IVCD interval can be initiated at that point rather than upon delivery of the pacing pulse.

Figure 10:
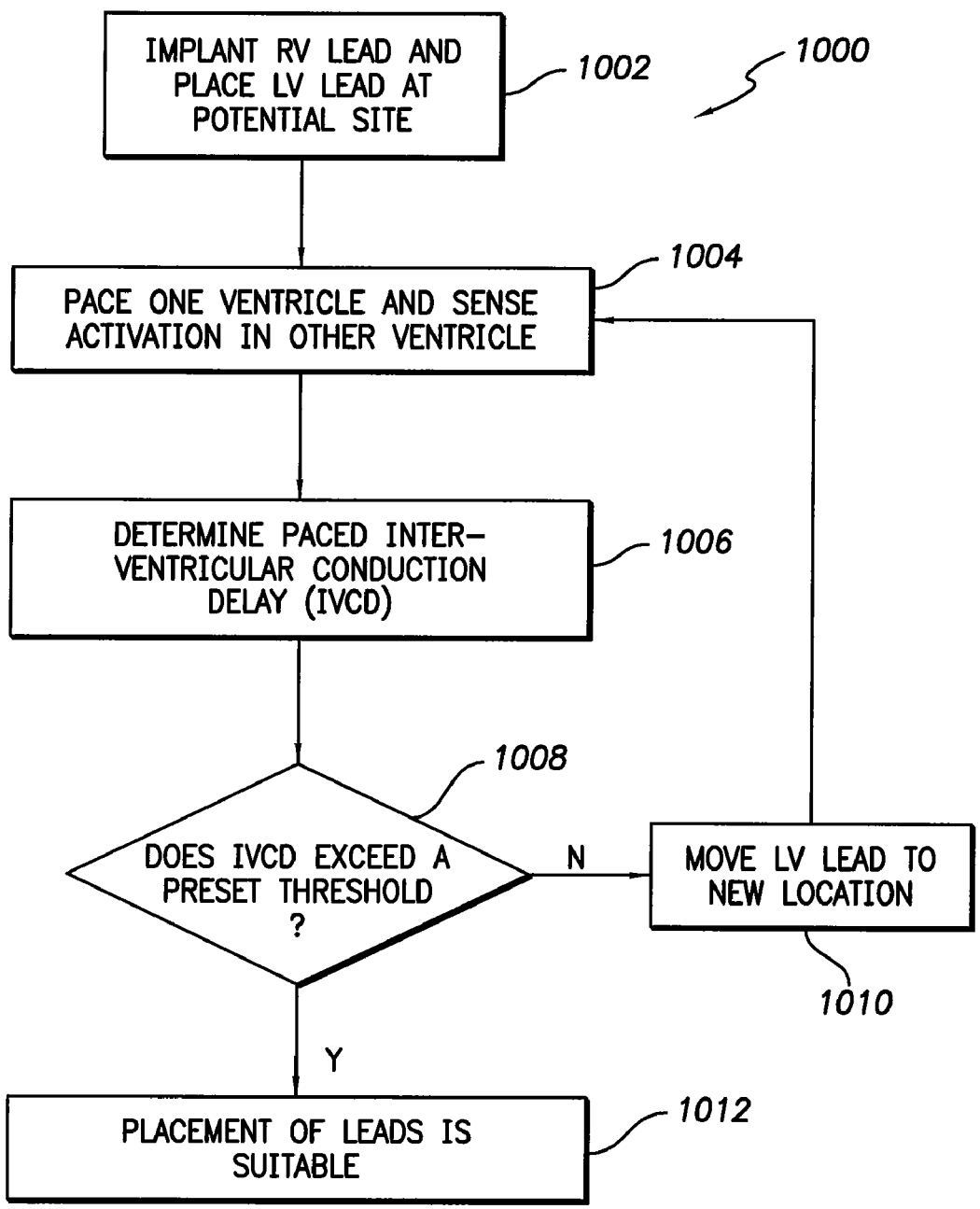
FIG. 10 is a flow chart of another exemplary method for determining whether electrode placement is suitable for CRT therapy.

Referring now to FIG. 10, an illustrative method is shown for determining the suitability of a particular lead placement. As already mentioned, IVCDs typically depend on electrode position and/or electrode configuration. Consequently, an IVCD may be used as one measure in determining an appropriate lead or electrode position or electrode configuration. At step 1002, the clinician implants an RV lead for stimulating the right ventricle, and locates an LV lead at a first potential site for sensing activity of the left ventricle (e.g., through the coronary sinus, epicardially, pericardially, etc.). At step 1004, a stimulation pulse is delivered to the left ventricle to cause the ventricle to depolarize, and RV activity is detected when the resulting depolarization waveform conducts from the left to the right ventricle. This embodiment is used for patients who suffer from LBBB or other left-sided conduction problems. For patients suffering from RBBB or other right-sided conduction problems, the right ventricle is paced and the corresponding activity is sensed in the left ventricle.

At step 1006, the interval between delivery of the stimulation pulse in the one ventricle and the sensed activity in the other ventricle is determined to be the IVCD. At decision block 1008, a determination is made whether the IVCD exceeds a threshold value. In one embodiment, the threshold value is on the order of 50 to 100 milliseconds, preferably about 80 milliseconds. Thus, if the IVCD does not exceed the threshold, operation proceeds to step 1010 and the system recommends to the clinician that one or both of the electrodes be moved to a new location. Once a new location or locations are found, operation returns to step 1004 and the process is repeated.

If, on the other hand, the IVCD value does exceed the threshold value, operation proceeds to step 1012 and the clinician is advised that the placement is suitable for CRT therapy. The clinician may then continue to implant the medical system and program the implantable medical device, including programming interval values for delivering CRT therapy.

As described above, for patients suffering from RBBB or other right-side conduction problems, the LV lead may be implanted in a desired location, and the RV lead may be advanced to a first potential site for testing, with the above-described method being carried out with LV pacing and RV sensing to determine IVCD values; if the IVCD value does not exceed a threshold value, the RV lead may be moved until a suitable IVCD value is identified. Alternatively, if the RV lead includes a plurality of electrodes, one or more different electrodes may be selected or, in general, an electrode configuration may be changed, the IVCD measured, compared to a threshold and then a decision made as to whether any further changes are warranted. A similar procedure may be used for an LV lead. Further, such techniques may be used if an epicardial electrode of other type of electrode is used for cardiac pacing.

Figure 11:
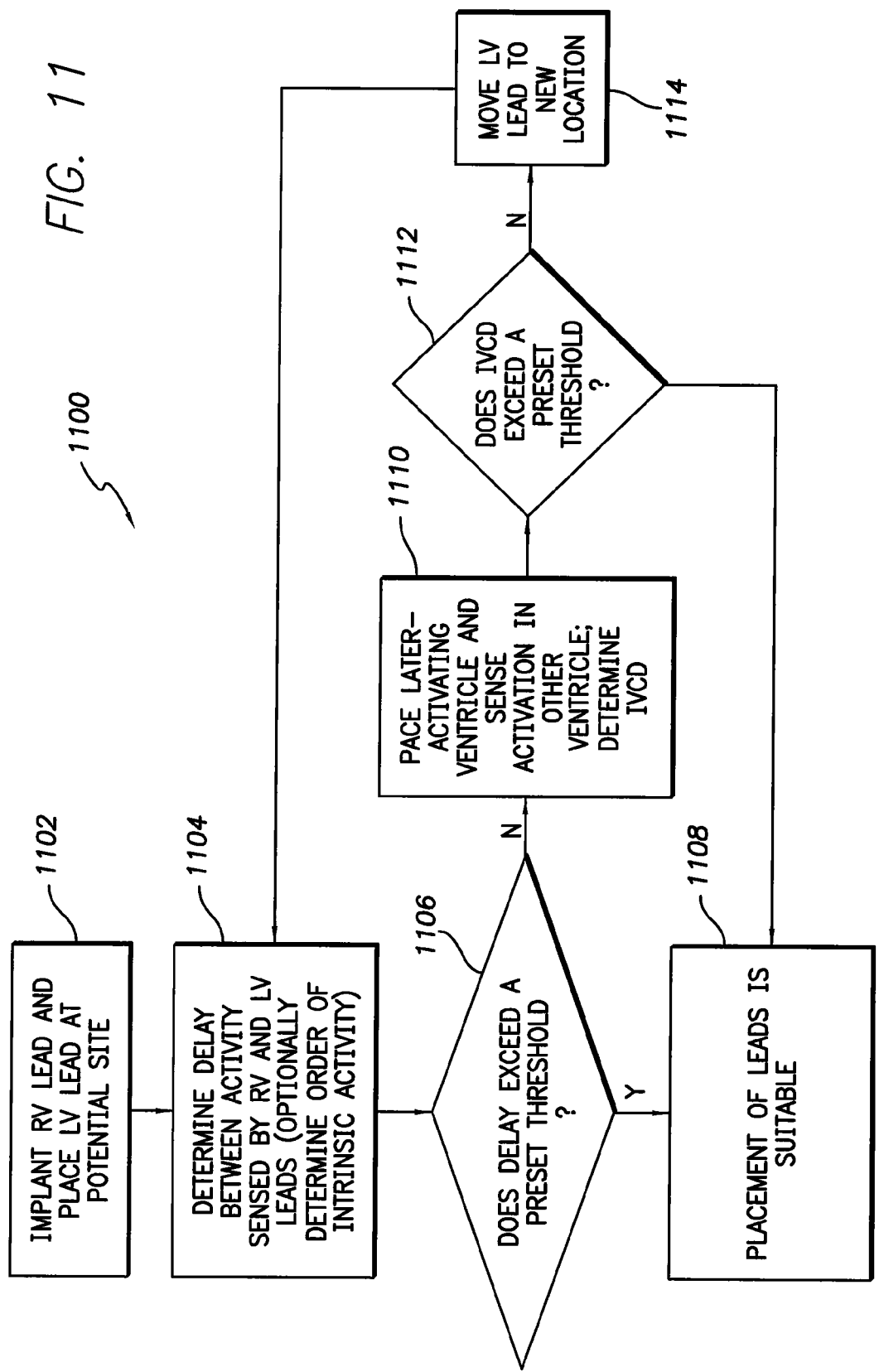
FIG. 11 is a flow chart of another exemplary method for determining whether electrode placement is suitable for CRT therapy

FIG. 11 shows a flow chart of a method for determining proper electrode placement according to another illustrative embodiment. According to the method, the electrodes are placed for communication with the RV and LV, respectively, at step 1102. In one embodiment, the clinician implants the RV lead in the right ventricle and the LV lead is advanced through the coronary sinus and into one of the coronary veins that overlie the left ventricle and into a first potential site to be tested. The clinician then connects the RV and LV leads to a suitable test device, for example, either the implantable medical device, an external pacing system analyzer, the programmer through a suitable adapter, or any other suitable device for processing the sensed IEGM data.

At step 1104, the intrinsic conduction delay 4 is determined based on the interval between activity detected in the RV and activity detected in the LV. For example, the test device may passively monitor the cardiac activity and detect intrinsic activity of the RV and LV, where the delay 4 is computed as the interval between RV and LV activation. In another embodiment, the test device determines an $AR_{RV}$ time and an $AR_{LV}$ time (or a $PR_{RV}$ time and a $PR_{LV}$ time) and computes Δ as the difference between the two values ($AR_{RV}$–$AR_{LV}$ or $PR_{RV}$–$PR_{LV}$).

At step 1104, the system optionally determines the order in which intrinsic activity was detected in the right and left ventricles (i.e., which ventricle experiences intrinsic activity first and which one experiences intrinsic activity last) if it has not already been determined a priori. For a patient known to have LBBB or RBBB, for example, this determination will not be necessary as the clinician already knows which ventricle is too slow in activating. This information can be used in step 1110 to determine which ventricle to pace and which ventricle to sense for determining an IVCD value, as described in greater detail below.

At decision block 1106, a determination is made whether 4 exceeds a threshold value, for example 30 msec. If so, operation proceeds to step 1108 and the placement is deemed suitable for CRT therapy. An optional message may be displayed on a user interface to indicate as such to the clinician.

In one embodiment, the delay value preferably exceeds a threshold value, which may range between about 20 and about 60 milliseconds, preferably about 30 milliseconds.

In another embodiment, the delay value is preferably within a range of values, for example between about 20 milliseconds and about 200 milliseconds, more preferably between about 30 and about 160 milliseconds. If the delay value does not exceed the lower limit of the range, operation proceeds to step 1110 as described below. In addition, if the delay value exceeds the upper limit of the range, then the system recommends that one or both of the electrodes be moved to new locations.

On the other hand, if 4 does not exceed the threshold value, operation instead proceeds to step 1110. At step 1110, the system determines the IVCD value by the following procedures:

1) delivering a stimulation pulse (preferably at a very short AV delay) to the ventricle that experienced intrinsic activity last;

2) sensing corresponding activity in the other ventricle (i.e., the ventricle that intrinsically activated first); and 3) determining an interval between either A) the delivery of the pulse in the first ventricle and detection of activity in the other ventricle, or B) verification of capture in the first ventricle and detection of activity in the other ventricle.

In one embodiment, where intrinsic activity is detected last in the LV, the pacing pulse is delivered to the LV in a subsequent cycle and at a short AV delay, and the conducted activity is sensed in the RV (IVCD-LR). Alternatively, where intrinsic activity is detected last in the RV, the RV is paced at a short AV delay and the conducted activity is sensed in the LV (IVCD-RL).

The IVCD is then compared with a threshold at query block 1112. The threshold may differ depending upon which interval calculation method was used. For example, the threshold can be on the order of about 60 to about 100 milliseconds, and preferably about 80 milliseconds, when the interval is between delivery of the pulse and detection of activity in the other ventricle. On the other hand, the threshold can be on the order of about 30 to about 50 milliseconds, and preferably about 40 milliseconds, when the interval is between verification of capture in the first ventricle and detection of activity in the other ventricle.

If the IVCD exceeds the threshold, then operation proceeds to step 1108 and the placement is considered suitable for CRT therapy. If not, operation proceeds to step 1114 and the clinician is alerted that one or more of the electrodes should be moved. In one embodiment, the clinician will move the LV lead, either to a new location within the same cardiac vein or withdraw it from the cardiac vein and then advance it through a different cardiac vein. Once the clinician has moved the lead to the next proposed location, operation returns to step 1104 and the process is repeated. If no suitable location is found after multiple sites are tested, the clinician may either withdraw the LV lead and implant an epicardial lead, or choose one of the tested sites and program the implantable medical device with the knowledge that the site may not be optimal for CRT therapy.

It will be understood by those skilled in the art that the sensing described herein can be done in a unipolar configuration, i.e., between an electrode implanted in the heart and the device housing, or in a bipolar configuration, i.e., between a pair of electrodes implanted in the heart. Bipolar sensing can be done with a truly bipolar lead (having a tip electrode and closely spaced ring electrode), or an integrated bipolar lead (having a tip electrode and a defibrillation coil used to sense electrical activity).

In an alternate embodiment, one or both of the RV and LV leads can be epicardial leads connected to the outside of the heart over the RV and LV, respectively, or one or both of the RV and LV leads can be replaced by satellite electrodes that telemeter information to a remote device.

As mentioned above, in some implant procedures the LV lead will be implanted prior to the RV lead, and it will be desirable to test the location of the LV lead, and possibly reposition it as necessary, prior to implanting the RV lead. In that case, a surface ECG signal may be used in place of the RV lead. In particular, a vector may be chosen that replicates the IEGM signal detected by an RV lead at the RV apex, for example lead V2, lead V1, lead V3, and/or lead II.

Figure 12:
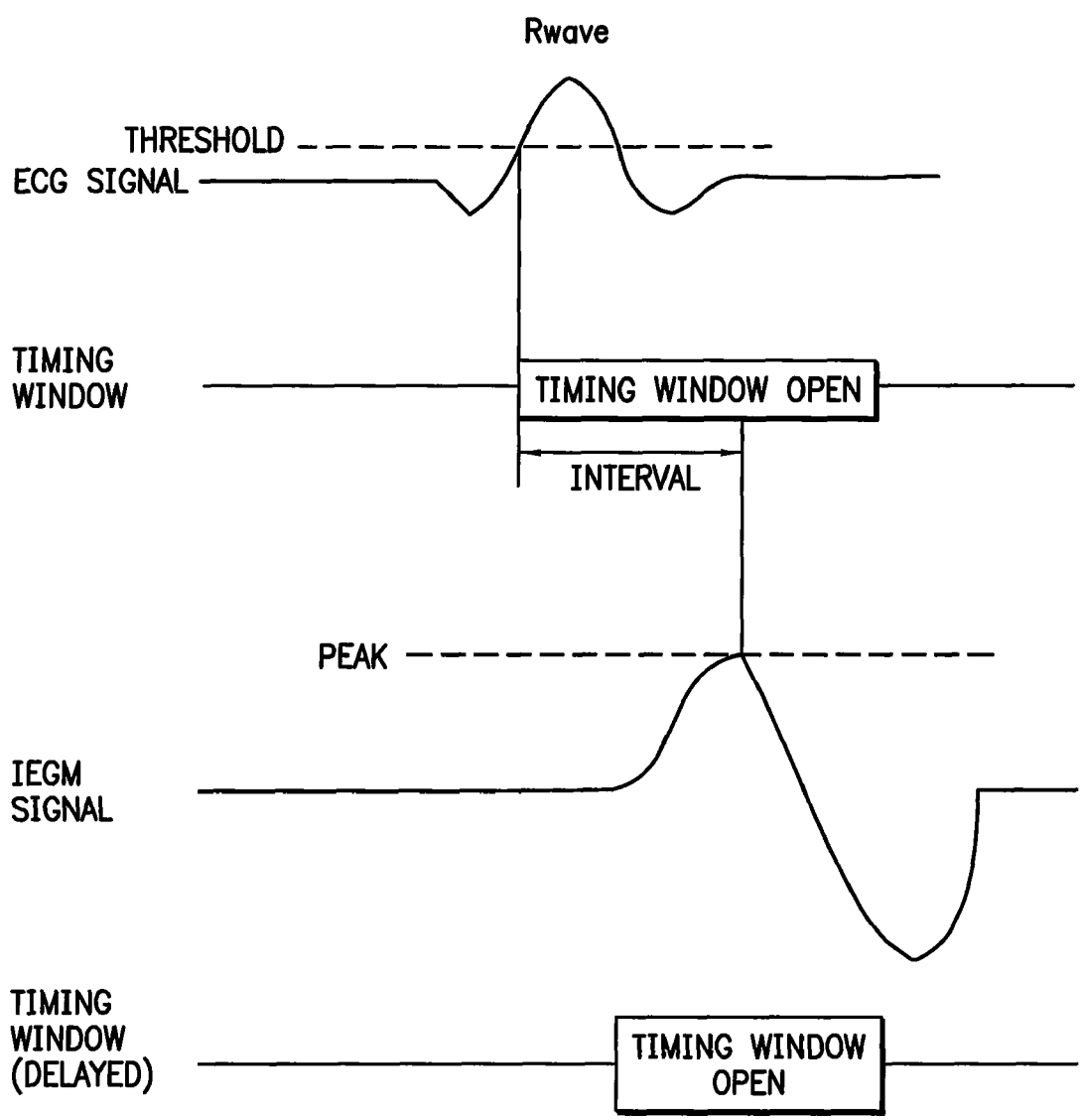
FIG. 12 is an exemplary plot of ECG and IEGM data to be used in accordance with another exemplary method.
Figure 13:
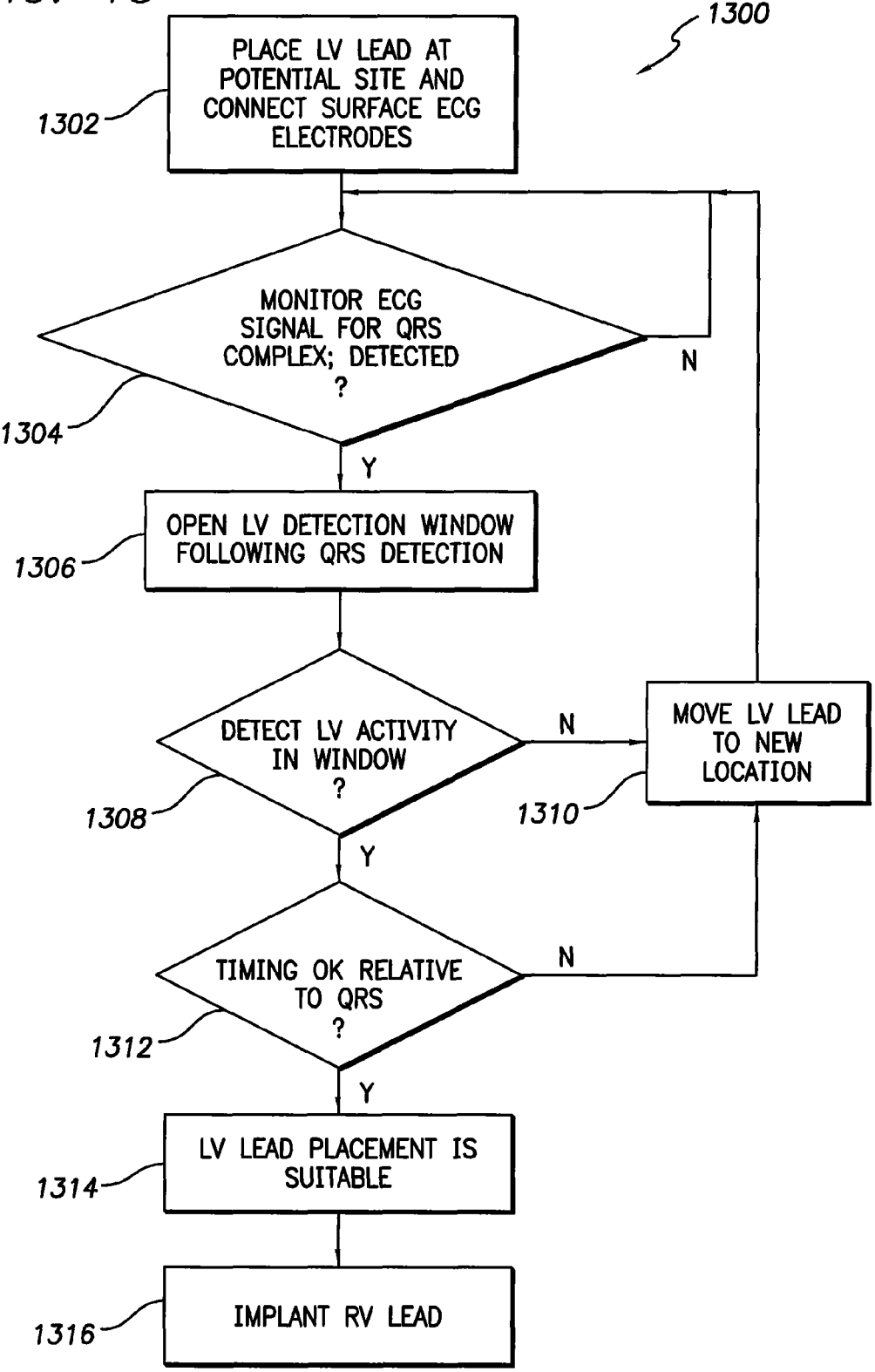
FIG. 13 is a flow chart of a method that uses the data from FIG. 12.

Referring to FIGS. 12 and 13, another embodiment is disclosed that addresses the situation where the LV lead is temporarily positioned and it is desired to test such placement prior to implanting the RV lead. As shown in FIG. 12, a surface ECG is preferably monitored to detect a QRS complex. Upon detection of the QRS complex (e.g., when the ECG signal exceeds the amplitude threshold), a timing window is opened to monitor for activity sensed by the LV lead. Preferably, the LV activity (in one embodiment detected by a peak of the LV activity signal) will occur toward the end of the window, corresponding to a sufficiently large Δ value; if it occurs too early in the window, the LV electrode placement will be deemed unacceptable for CRT therapy. An interval 1202 (corresponding to the Δ value) may be computed between detection of ventricular activity from the ECG signal and corresponding left ventricular activity detected by the IEGM signal. The interval may be compared with a threshold, as described in detail above.

Alternatively, the window may be delayed following the detection of the QRS complex (see the Timing Window (alternate)), for example approximately 30 milliseconds, and if no activity is detected within the window, then the activity either occurs too early or too late and another site is recommended. If activity is detected within the window, then the electrode placement is deemed suitable.

As shown in FIG. 13, operation begins at step 1302 with the clinician locating the LV lead at a first potential site, and attaching the surface ECG electrodes to the patient. At query block 1304, the system monitors the ECG signal for a QRS complex. Upon detection of the QRS complex, operation proceeds to step 1306, and the system opens a window to monitor the LV lead for detection of left ventricular activity. As described above, the window may be opened immediately following the QRS detection, or be delayed a predetermined period of time.

At query block 1308, if no LV activity is sensed within the window, then operation proceeds to step 1310 and a different placement is recommended for the LV electrode. On the other hand, if LV activity is detected within the window, operation proceeds to optional step 1312, where the timing of the LV activity is compared to the QRS detection. As mentioned above, when the opening of the window is delayed following QRS detection, step 1312 is unnecessary. If the window is opened immediately following QRS detection, then step 1312 is preferably included. If the timing of the LV activity relative to the QRS detection (e.g., if the interval between QRS detection and LV activity is sufficiently long) then operation proceeds to step 1314 and the electrode placement is deemed suitable. If not, operation instead proceeds to step 1310 and a different electrode placement is recommended.

Once the LV site is selected, operation proceeds to step 1314, and the RV electrode is implanted in the RV. In one embodiment, the RV electrode is placed using the ECG and LV IEGM information as a reference. Alternatively, the RV electrode location can be selected to further increase the separation between detected RV activity and LV activity.

It will be understood by those skilled in the art that the analysis of the electrode placement can be performed by any device that is able to receive electrical signals from the electrodes and process the signals to determine cardiac timing information. For example, the method can be carried out by the implanted pacemaker or defibrillator, which analyzes the information and then may telemeter such information to a programmer or other external device. In addition, the electrodes may be temporarily connected to a pacing system analyzer (PSA), directly to the programmer, or to any other device capable of processing the sensed cardiac activity.

It will be understood by those skilled in the art that while the various embodiments are described primarily for patients who suffer from LBBB and who therefore have late-acting left ventricles, the same embodiments can be applied to patients who suffer from RBBB and who therefore have late-acting right ventricles. In those patients, the various embodiments are applied in reverse, i.e., 1) the LV lead is implanted, 2) the RV lead is located at a potential site, 3) the Δ value and/or IVCD value are determined, and 4) to RV lead is moved to a new site if the Δ value and/or IVCD value do not exceed the respective threshold(s).

In yet another embodiment, the system may determine a 4 value, an IVCD value for right ventricular pacing and left ventricular sensing (IVCD-RL), and an IVCD value for left ventricular pacing and right ventricular sensing (IVCD-LR). Only if each value exceeds a corresponding threshold will the location(s) be deemed suitable; if not, one or both of the RV and LV electrodes will be moved to new locations, and the values recalculated.

The above-described method for improving response to CRT therapy can also be used for other features utilized by implantable cardiac devices. Consider a technique that uses such timing parameters (A, IVCD-RL, IVCD-LR) and one or more corresponding thresholds to decide whether beat-to-beat capture detection may be suitably performed or to decide whether a specialized capture detection method may be implemented.

In general, capture detection techniques deliver energy to the myocardium using a selected electrode configuration and then sense electrical activity of the myocardium using at least one electrode of the electrode configuration. For example, if energy is delivered using a tip electrode and ring electrode of an RV lead (see, e.g., FIG. 1), then sensing usually occurs using these two electrodes (e.g., bipolar sensing) or using one of these electrodes and, for example, a can electrode (e.g., unipolar sensing). The use of at least one energy delivery electrode for sensing ensures that the sensed information includes information local to the site of energy delivery. As many capture detection techniques can also determine or estimate capture thresholds, local information is of particular value in understanding how myocardial tissue responds to delivered energy.

With respect to capture detection or verification, consider biventricular capture verification, and especially beat-to-beat, biventricular capture verification. As will be apparent to those skilled in the art, if the 4 value is too small, an evoked response sensed in a first chamber may be corrupted by applied stimulation in the second chamber causing fusion, or by far-field sensing in the first chamber of the applied stimulus. As described herein, if IVCD-RL or IVCD-LR is too small (e.g., electrodes/leads too close), then the likelihood of a sensed evoked response for one ventricle appearing fused with and an evoked response for the other ventricle increases. As conventional capture detection algorithm usually rely on characteristics of an evoked response to distinguish capture from non-capture, such fusion can confound capture detection. For example, such fusion may alter an evoked response signal's derivative value (e.g., $D_{Max}$) and/or an integral value (e.g., PDI).

Therefore, the methods described herein may be used to determine whether an existing electrode placement is suitable for performing biventricular capture verification. In various examples, a method may be also used to determine whether one or more electrodes should be moved in order to improve the likelihood of being able to successfully perform capture verification. Alternatively, or in addition to, where feasible, a change may occur in an electrode configuration for delivery of energy to the myocardium. Noting that a change in myocardial condition may also cause a change in an IVCD and that such information may be useful to assess myocardial condition.

Thus, in one embodiment for use in connection with biventricular capture verification, the right-sided electrode and left-sided electrode are placed, and the IVCD value is measured. If the IVCD exceeds a preset threshold (e.g., one or more of the thresholds described above), then the placement is considered suitable for performing biventricular capture verification. If not, either 1) a clinician is alerted that one or more of the electrodes should be moved, 2) the clinician is advised that biventricular capture verification should not be performed given the electrode spacing, or 3) the implanted device may automatically disable the biventricular capture verification feature. Thus, the clinician may move the left-side electrode, with the process being repeated until a suitable spacing is found.

Various exemplary methods pertaining to capture verification, sometimes referred to as capture detection, are described with respect to FIGS. 14-22. To understand better principles of capture FIG. 14 shows a capture detection and energy threshold search method 1400 and a plot 1402 of pulse amplitude versus pulse duration and a "strength-duration" curve 1410. The method 1400 relies on capture detection (i.e., capture verification). Referring to the plot 1402, if stimulation energy falls to the left of and/or below the curve 1410, it will be subthreshold for purposes of eliciting an evoked response and there will be loss of capture. If stimulation energy coincides with or falls to the right and/or above of the curve 1410, capture should be present. The strength-duration curve 1410 indicates that pulse amplitude must be high for extremely narrow pulse width or short duration to cause capture. At some point, typically around 1 ms, the pulse amplitude plateaus and does not decrease further despite additional increases in pulse duration. The plateau is typically referred to as the rheobase and the threshold at twice the rheobase is typically referred to as the chronaxie point.

Some pacing systems use algorithms that aim to automatically adjust output and/or assess capture threshold, usually on a periodic basis. As these algorithms rely on detection of verification of capture, they are referred to as capture detection algorithms. A particular system uses the AUTOCAPTURE™ algorithm (St. Jude Medical, Cardiac Rhythm Management Division, Sylmar, Calif.) to automatically monitor capture on a beat-by-beat basis, provide a high output back-up pulse in the setting of loss of capture associated with the primary output pulse and adjust output and/or assess capture threshold on both a scheduled and on an as-needed basis.

The method 1400 illustrates a basic threshold search that relies on capture detection, which may be part of a beat-to-beat or other capture detection algorithm. Again, where capture is not detected, i.e., loss of capture, corrective action is typically required, for example, a change in pulse amplitude (per plot 1402), a change in pulse duration (per plot 1402), etc.

The method 1400 commences in a start block 1454, where an implantable device may be programmed to perform capture detection and a threshold search. In some instances, a threshold search is performed on a periodic basis, whether loss of capture has been detected or not. Such a threshold search may help ensure adequate capture as well as battery life. The method 1400 continues in a decision block 1458 that decides if loss of capture occurred based on sensed cardiac activity. If the decision block 1458 decides that loss of capture did not occur, then the method continues at the start block 1454. However, if loss of capture occurred, then the method 1400 continues at an adjustment block 1462 that adjusts energy delivery. For example, the adjustment block 1462 may increase amplitude of a stimulation pulse and/or increase duration of a stimulation pulse.

Another decision block 1466 follows that decides if a pulse delivered using the adjusted energy caused capture. If the decision block decides that capture did not occur, then the method 1400 returns to the adjustment block 1462, or it may take other action. However, if capture did occur, then the method 1400 continues at a search block 1470 that seeks a capture threshold, for example, as indicated by a point or points on the line 1410 of the plot 1402. After the threshold search 1470, the method 1400 may return to the decision block 1458 or it may take other action as appropriate. In general, such algorithms place patient safety ahead of battery current drain; however, when the chronic threshold is low, such an algorithm may also minimize battery current drain, effectively increasing device longevity.

In addition to beat-to-beat capture verification, the AUTOCAPTURE™ algorithm runs a capture threshold assessment test once every eight hours. To perform this test, the paced and sensed AV delays are temporarily shortened to about 50 ms and to about 25 ms, respectively. The AUTOCAPTURE™ algorithm generally uses a bottom-up approach (also referred to as an "up threshold") and a back-up pulse for safety when an output pulse does not result in capture. With respect to use of a back-up pulse, an output pulse of about 4.5 volts is typically sufficient to achieve capture where lead integrity is not an issue. Use of a back-up pulse may also adequately benefit certain patients that are quite sensitive to loss of capture. For example, patients having a high grade AV block may be sensitive to protracted asystole. Even if loss of capture is recognized immediately and adjustment is completed in less than about 1 second, a patient may still have been asystolic for over 2 seconds utilizing a standard capture threshold test without a back-up. A back-up pulse typically prevents occurrence of such a long asystolic period. However, most conventional autocapture threshold/detection algorithms do not attempt to detect the evoked response directly related to capture of the back-up. Thus, the assumption that a back-up pulse resulted in capture is generally not tested. Various exemplary methods described herein optionally include evoked response detection of the back-up pulse to help determine if a back-up pulse caused an evoked response thus confirming the presence of capture associated with this stimulus. Such ER or capture detection may be implemented for a unipolar back-up pulse, a bipolar back-up pulse or other type of back-up pulse.

In general, the term "sensing" is often utilized with respect to an implantable cardiac stimulation therapy device (e.g., a pacemaker) recognizing native atrial and/or ventricular depolarizations. While technically, detection of an evoked response (ER) relies on or includes "sensing", an implantable device often uses a separate circuit for ER detection. Throughout, the term "ER detection" or "capture detection" may be used in place of sensing when specifically concerned with, for example, a capture algorithm and recognition of capture.

With respect to ER detection, various exemplary methods may use a unipolar primary pulse with bipolar ER detection, a unipolar primary pulse with unipolar ER detection, a bipolar primary pulse with bipolar ER detection, a bipolar primary pulse with unipolar ER detection and/or no primary pulse ER detection. Various exemplary methods may use a unipolar back-up pulse with bipolar ER detection, a unipolar back-up pulse with unipolar ER detection, a bipolar back-up pulse with bipolar ER detection, a bipolar back-up pulse with unipolar ER detection and/or back-up pulse ER detection.

Regarding AUTOCAPTURE™ algorithms, the first generation algorithm was implemented using a unipolar output configuration and a bipolar detection configuration. Where insulation and/or fracture issues arise for a proximal conductor (bipolar detection), an evoked response may not be sensed and, in turn, result in delivery of a high voltage back-up pulse and a ramping up of the primary output voltage (e.g., energy via voltage, pulse width, etc.). A capture threshold history may exhibit some information that relates to such a problem. In particular, a history may help to identify intermittent problems (e.g., sporadic increases in reported capture threshold where the actual unipolar capture threshold is relatively stable).

In clinical follow-up, a care provider may perform a threshold test to determine if the algorithm for capture is working properly and for further assessment. In systems that use the AUTOCAPTURE™ algorithm, a follow-up clinical test includes automatically and temporarily setting PV delay and AV delay intervals to about 25 ms and about 50 ms, respectively. Shortening of the AV and PV delays acts to minimize risk of fusion. Fusion (of any type) may compromise measurement and detection of an ER signal, especially ER signal amplitude. If results from the follow-up test indicate that enabling of the algorithm would not be safe due to too low an evoked response or too high a polarization signal, then the algorithm may be disabled and a particular, constant output programmed to achieve capture with a suitable safety margin.

If the ER and polarization signals are appropriate to allow an autocapture algorithm to be enabled, an ER sensitivity will be recommended by the programmer and may then be programmed as it relates to detection of an ER signal. As described herein, a measure such as IVCD may be used and, in various examples, other information (e.g., too low an evoked response or too high a polarization signal) may be used as well to enable or disable a capture detection algorithm.

The follow-up tests typically work top down. If loss of capture occurs, a first output adjustment step typically sets a high output and then decreases output by about 0.25 volts until loss of capture occurs (also referred to as a "down threshold"). At this point, output is increased in steps of a lesser amount (e.g., about 0.125 volts) until capture occurs. Once capture occurs, a working or functional margin of about 0.25 volts is added to the capture threshold output value. Hence, the final output value used is the capture threshold plus a working margin. Systems that use a fixed output use a safety margin ratio instead of an absolute added amount. The safety margin is a multiple of the measured capture threshold, commonly 2:1 or 100% to allow for fluctuations in the capture threshold between detailed evaluations at the time of office visits.

With respect to a down threshold approach, in instances where loss of capture occurs, a first output adjustment step typically increases output until capture is restored. Steps used in the AUTOCAPTURE™ algorithm are typically finer than those used in a routine follow-up capture threshold test. At times, a down threshold algorithm may result in a threshold that is as much as 1 volt lower from the result of an up threshold algorithm. This has been termed a Wedensky effect. In general, an actual output setting (e.g., including safety margin) may be adjusted to account for whether a patient is pacemaker dependent. In a patient who is not dependent on the pacing system, a narrower safety margin may be selected than would be the case for a patient whom the physician considers to be pacemaker dependent.

As already mentioned, lead instability may affect capture threshold, similarly, capture threshold history may help to identify lead instability. Lead instability includes issues germane to failure as well as issues germane to movement of a lead (e.g., to cause movement of an electrode of the lead, etc.). A stable capture threshold history may indicate normal lead function. However, marked fluctuations in capture threshold over time may indicate a lead stability problem, such as movement and variations with the degree of contact between the electrode and myocardial tissue. If the problem is associated with movement, repositioning or re-anchoring may be required. If such fluctuations occur in the early post-implant period, the problem may relate to positional instability as opposed to a marked inflammatory reaction at the electrode-tissue interface (e.g., "lead maturation"). As described herein, various exemplary methods may distinguish positional instability issues from lead failure issues (e.g., mechanical degradation, etc.). Such exemplary methods may include use of capture threshold information and optionally information such as IVCD (e.g., IVCD-RL and/or IVCD-LR).

As can be appreciated by the foregoing discussion on capture detection, when delivery of stimulation energy occurs to both ventricles, then adjustments to timing parameters, etc., may affect cardiac performance and cause discomfort, especially for a patient that relies on bi-ventricular pacing. In addition, as already mentioned, fusion may confound capture detection. For example, where left and right ventricles contract without any significant delay, sensing electrodes may not be able to sense separate waveforms, but rather a fused waveform. In turn, a capture detection may not be able to detect capture give such a fused waveform (e.g., for one or both ventricles). Thus, an interplay exists between timing parameters, placement/condition/type of sensing electrodes and conductive substrate (e.g., the myocardium and fluid).

Various exemplary methods, devices, systems, etc., described herein address issues that can arise due to such interplay. To more fully appreciate these technologies, a discussion of fusion follows.

Fusion is typically characterized by a wave complex formed by depolarization of the myocardium initiated by two different foci, commonly a non-intrinsic stimulus as from a pacemaker or ICD and an intrinsic stimulus. Of course, fusion may appear different depending on point of observation or sensing. For example, if a sensing electrode is positioned near and/or between the two foci, then it may sense a waveform that does not clearly distinguish contributions from each focus. Where bi-ventricular pacing occurs, then two foci exist, one for each ventricle. However, other types of multiple foci may exist. Table 1, below, sets forth various fusion scenarios where stimuli and/or consequences thereof may cause fusion.

TABLE 1

Exemplary Fusion Scenarios

| Scenario | Stimulus | Fusion Chamber | Parameters |
|---|---|---|---|
| 1 | P or A to RV; pace RV | RV | $AVF_{RV}/PVF_{RV}$ |
| 2 | P or A to LV; pace LV | LV | $AVF_{LV}/PVF_{LV}$ |
| 3 | P or A to RV conduct to LV; pace LV | LV | Various |
| 4 | P or A to LV conduct to RV; pace RV | RV | Various |
| 5 | RV pace conduct to LV; pace LV | LV/RV | VVF – RL $AVF_{RV}/PVF_{RV}$ |
| 6 | LV pace conduct to RV; Pace RV | RV/LV | VVF – LR $AVF_{LV}/PVF_{LV}$ |

In Table 1, Scenario 1 is for fusion in the right ventricle where a paced stimulus to the right ventricle ($V_{RV}$) fuses with an intrinsic or non-intrinsic atrial stimulus conducted to the right ventricle ($R_{RV}$); Scenario 2 is for fusion in the left ventricle where a paced stimulus to the left ventricle ($V_{LV}$) fuses with an intrinsic or non-intrinsic atrial stimulus conducted to the left ventricle ($R_{RV}$); Scenario 3 is for fusion in the left ventricle where a paced stimulus to the left ventricle ($V_{LV}$) fuses with an intrinsic or non-intrinsic atrial stimulus conducted to the right ventricle ($R_{RV}$) and is delayed in conduction to the left ventricle ($R_{c-LV}$) (e.g., where left bundle branch block may exist and delay conduction of the atrial stimulus to the left ventricle); Scenario 4 is for fusion in the right ventricle where a paced stimulus to the right ventricle ($V_{RV}$) fuses with an intrinsic or non-intrinsic atrial stimulus conducted to the left ventricle ($R_{LV}$) and is delayed in conduction to the right ventricle ($R_{c-RV}$) (e.g., where right bundle branch block may exist and delay conduction of the atrial stimulus to the right ventricle); Scenario 5 is for fusion in the left ventricle where a paced stimulus to the left ventricle ($V_{LV}$) fuses with a paced stimulus to the right ventricle ($V_{RV}$) that subsequently conducts to the left ventricle ($ER_{c-LV}$) and optionally for fusion in the right ventricle where the paced stimulus to the right ventricle ($V_{RV}$) fuses with an intrinsic or non-intrinsic atrial stimulus; and Scenario 6 is for fusion in the right ventricle where a paced stimulus to the right ventricle ($V_{RV}$) fuses with a paced stimulus to the left ventricle ($V_{LV}$) that subsequently conducts to the right ventricle ($ER_{c-}$ $RV$) and optionally for fusion in the left ventricle where the paced stimulus to the left ventricle ($V_{LV}$) fuses with an intrinsic or non-intrinsic atrial stimulus. Thus, Scenarios 5 and 6 can may result in detection of fusion in both ventricles.

Table 1 also shows various parameters that may be determined for the various scenarios. AVF and PVF refer to surrogates or substitutes for AR and PR and VVF-RL and VVF-LR refer to surrogates or substitutes for IVCD-RL and IVCD-LR, which are discussed above. Where "various" is listed in Table 1, sensing and/or other circumstances may determine which parameters may be determined or estimated. In the scenarios 3 and 4, an AR or PR may be determined for one ventricle and an AVF or PVF for the other ventricle.

Various exemplary methods, devices, systems, etc., may optionally rely on occurrence of fusion or other interference to determine one or more pacing parameters and/or to decide whether to enable a capture detection algorithm (e.g., beat-to-beat, tiered, etc.). In particular, a variety of techniques may be used to analyze cardiac activity for fusion or other interference. Such techniques include traditional fusion detection techniques that rely on derivative (e.g., slope, acceleration, etc.), amplitude, integral, morphology, etc. For example, morphology discrimination may be used to detect fusion. Morphology discrimination typically relies on "dynamic template matching" to discriminate between normal and abnormal events (e.g., fusion, intrinsic depolarization, non-intrinsic depolarization, etc.), which may be present in sensed cardiac activity. Morphology discrimination enables a device to examine multiple characteristics of an electrogram (e.g., sensed cardiac activity), as opposed to techniques which may look only at a complex's width, amplitude and/or slew rate; however, such techniques may be used in conjunction with or as alternatives to one or more morphology discrimination techniques. Morphology discrimination allows for a comparison between a complex, or portion thereof, and a template. For example, morphology discrimination may compare a last acquired complex with a predetermined physician-selected patient-specific template. In commercially available implementations of morphology discrimination (MD), a MD algorithm is normally disabled in the setting of a delivered output pulse. In contrast, various exemplary methods described herein may allow for morphology discrimination or other signal characterization following delivery of an output pulse.

Various exemplary methods, devices, systems, etc., described herein may use scenarios 3 and 4. In particular, an exemplary method aims to cause scenario 3 or scenario 4 to be present, thus, fusion may be intentional. While the site of fusion is referred to as "LV" or "RV", the site of fusion may be located and optionally controlled. Fusion may optionally occur at the intraventricular septum (IVS). Intentional or controlled fusion may provide benefits, especially for patients subject to cardiac resynchronization therapy (CRT).

An exemplary method may cause fusion per scenario 3 or scenario 4 to determine a threshold for use in deciding whether to enable beat-to-beat capture detection or another type of capture detection. For example, such a method may intentionally cause fusion, enable a capture detection algorithm and then decide if the capture detection algorithm can adequately detect capture given the intentional fusion.

Figure 15:
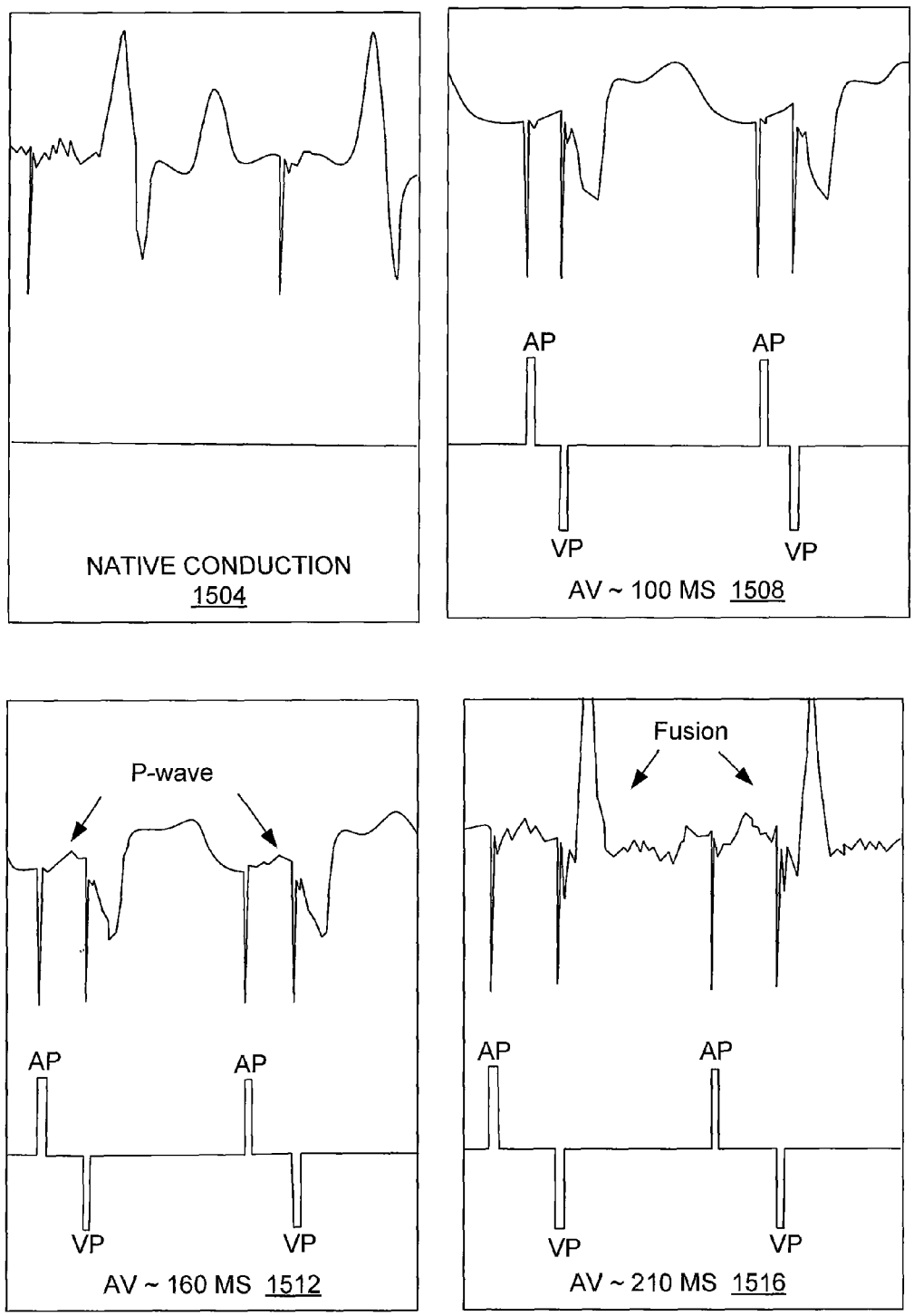
FIG. 15 is a series of plots that illustrate capture waveforms and fusion waveforms for various pacing parameter values.

To understand better the relationship between pacing parameters, bi-ventricular synchrony and fusion, FIG. 15 shows four ECGs 1504, 1508, 1512, 1516, which correspond to different scenarios. The ECG 1504 corresponds to no pacing where native conduction controls, directly or indirectly, contraction of the right ventricle and the left ventricle. The ECG 1508 corresponds to pacing with an AV interval of 100 ms, which is a nominal shipped value for a commercially available biventricular pacemaker). The ECG 1508 shows that, for an AV interval of 100 ms, there was total loss of AV synchrony. The ECG 1512 corresponds to pacing with an AV interval of 160 ms. The ECG 1512 shows that the P wave becomes visible in front of the paced evoked response complex and that the paced evoked response complex narrows. The narrowest paced evoked response complex appears in the ECG 1516, where an AV interval of 210 ms provided the best velocity time integral (echo measure of stroke volume), which also resulted in fusion with native conduction down the right bundle.

The plot 1512 indicates that fusion may be readily experienced in bi-ventricular pacing therapy. Thus, decisions should be made as to capture detection to address the possibility of such situations.

As described herein, various methods for determining pacing parameters such as VV delay may also reduce risk of fusion from bi-ventricular stimuli. For example, where $VV=0.5 (\Delta+\Delta_{IVCD})$ where $\Delta$ is the intrinsic conduction time delay to RV and LV leads and $\Delta_{IVCD}$ is the correction term from the difference in IVCD-RL and IVCD-LR, risk of fusion is reduced or eliminated. Trials performed using this VV technique showed that paced fusion occurred when the VV parameter was set greater than a parameter $VV_{PF}$, which was a percentage of the IVCD (e.g., canine trials indicated a large fraction of IVCD). Hence, where the VV delay parameter is set according to such a method, the likelihood of fusion is greatly reduced or eliminated if $VV<<VV_{PF}$. In general, as VV delay increases (e.g., with respect to IVCD) the risk of wavefronts fusing increases.

An exemplary method includes determining an IVCD by pacing one ventricle and sensing at the other non-paced ventricle. Where IVCD is less than a threshold, for example, about 80 ms, then the RV and LV leads (or electrodes) may be too close to each other for purposes of beat-to-beat capture detection per, for example, the aforementioned AUTOCAPTURE™ algorithm. Where a patient already has an implanted device, then a decision may be made to disable the capture detection during bi-ventricular pacing therapy. However, if such information is acquired at the time of implant, then repositioning may occur for a LV lead or RV lead, until the criteria of appropriate lead position is found. In another example, a patient has an implanted device where alternative electrode configurations may be selected. In this example, such alternatives may be tested with respect to one or more criteria to render a decision as to capture detection for that patient. Of course, such alternative electrode configurations should be suitable for delivery of pacing therapy.

With respect to techniques for reducing risk of fusion that may interfere with capture detection, an exemplary method decides if VV delay is less than an IVCD minus pacing latency (PL) and minus some additional delay, which may be represented by the equation: $VV<IVCD-PL-40$ ms (e.g., where the additional delay is about 40 ms). In another example, an equation is used to set the parameter $\Delta$ equal to IVCD minus pacing latency and optionally some additional delay (e.g., about 40 ms): $\Delta=IVCD-PL-40$ ms. Pacing latency is a time delay that may be measured from the time of delivering a pacing pulse to a minimum in an ER (or maximum, depending on configuration) or to the onset of ER or to the maximum slope (e.g., $D_{MAX}$), etc.

As already mentioned, VV may equal $0.5 (\Delta+\Delta_{IVCD})$ (or $\alpha((\Delta+\Delta_{IVCD}))$ and for some patients, the value of $\Delta_{IVCD}$ is negligible. Consider an example where $\Delta=PR_{LV}-PR_{RV}$. In general, the sinus node initiates contraction of the heart. Thus, the PR terms may be broken into a sinus node to septum segment and a septum to ventricle segment. For $PR_{LV}$ and $PR_{RV}$, the segment from the sinus node to the septum may be considered the same. Hence, Δ may be represented as the difference between the septum to ventricle for the left ventricle (LS) minus that for the right ventricle (RS).

Figure 21:
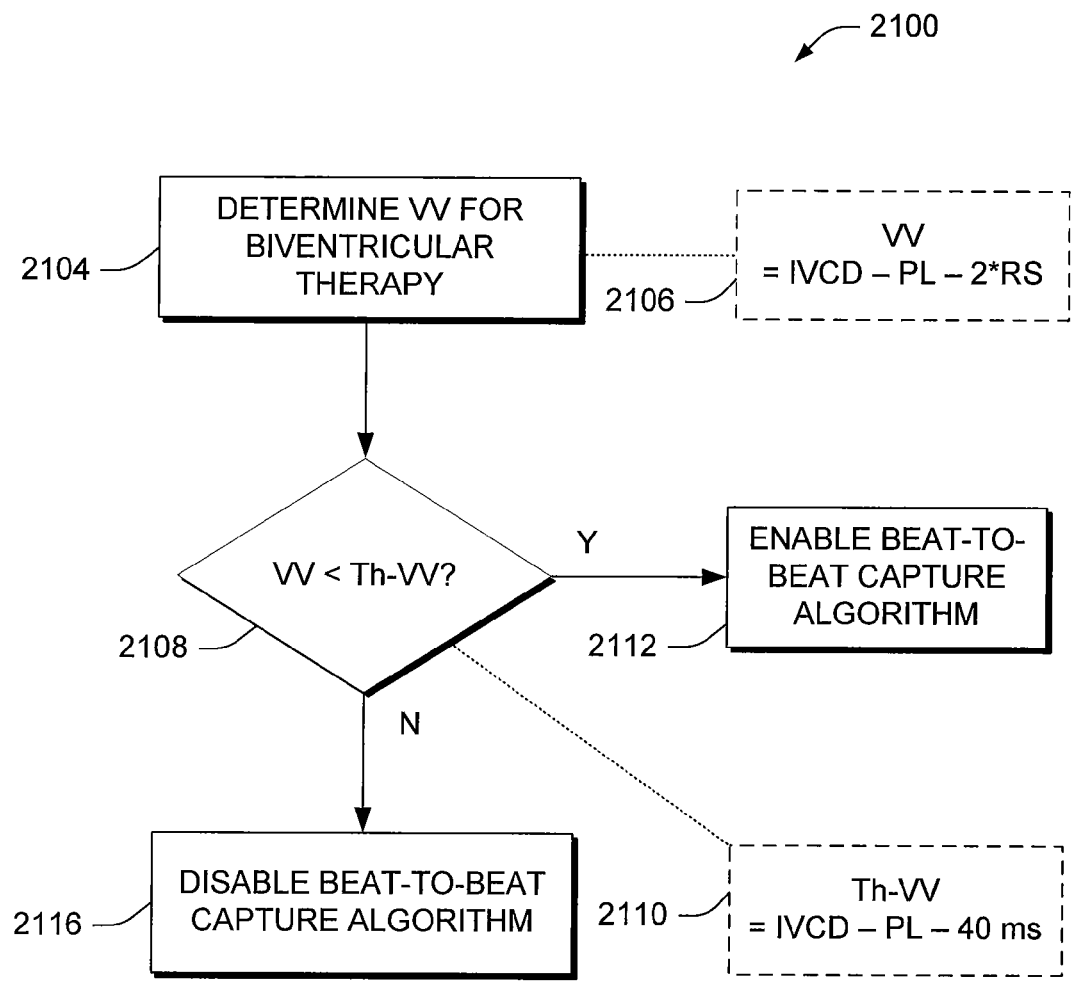
FIG. 21 is a flow chart of an exemplary method for deciding whether an interventricular conduction interval is suitable for performing bi-ventricular, beat-to-beat capture detection.

Given the parameter RS (e.g., a delay from septum to an RV lead), a criterion for Δ may be given as IVCD−pacing latency−2*RS. Where VV=0.5*Δ, by substitution, VV=0.5*(IVCD−pacing latency−2*RS) and this value may be selected or determined to be less than IVCD−pacing latency−an additional delay (e.g., approximately 40 ms). After some algebraic operations, 0.5*Δ+RS>40 ms (i.e., the additional delay) is a criterion that can be used for determining a VV delay where risk of fusion is minimal and where beat-to-beat capture detection may be implemented. The parameter RS can be calculated using Δ and IVCD where Δ=IVCD−pacing latency−2*RS. With RS and Δ known, a decision can be made to determine whether beat-to-beat capture can be reliably implemented for bi-ventricular pacing. FIG. 21, described further below, shows an exemplary method 2100 that may use the aforementioned equation for VV and/or the aforementioned equation for Δ.

Figure 16:
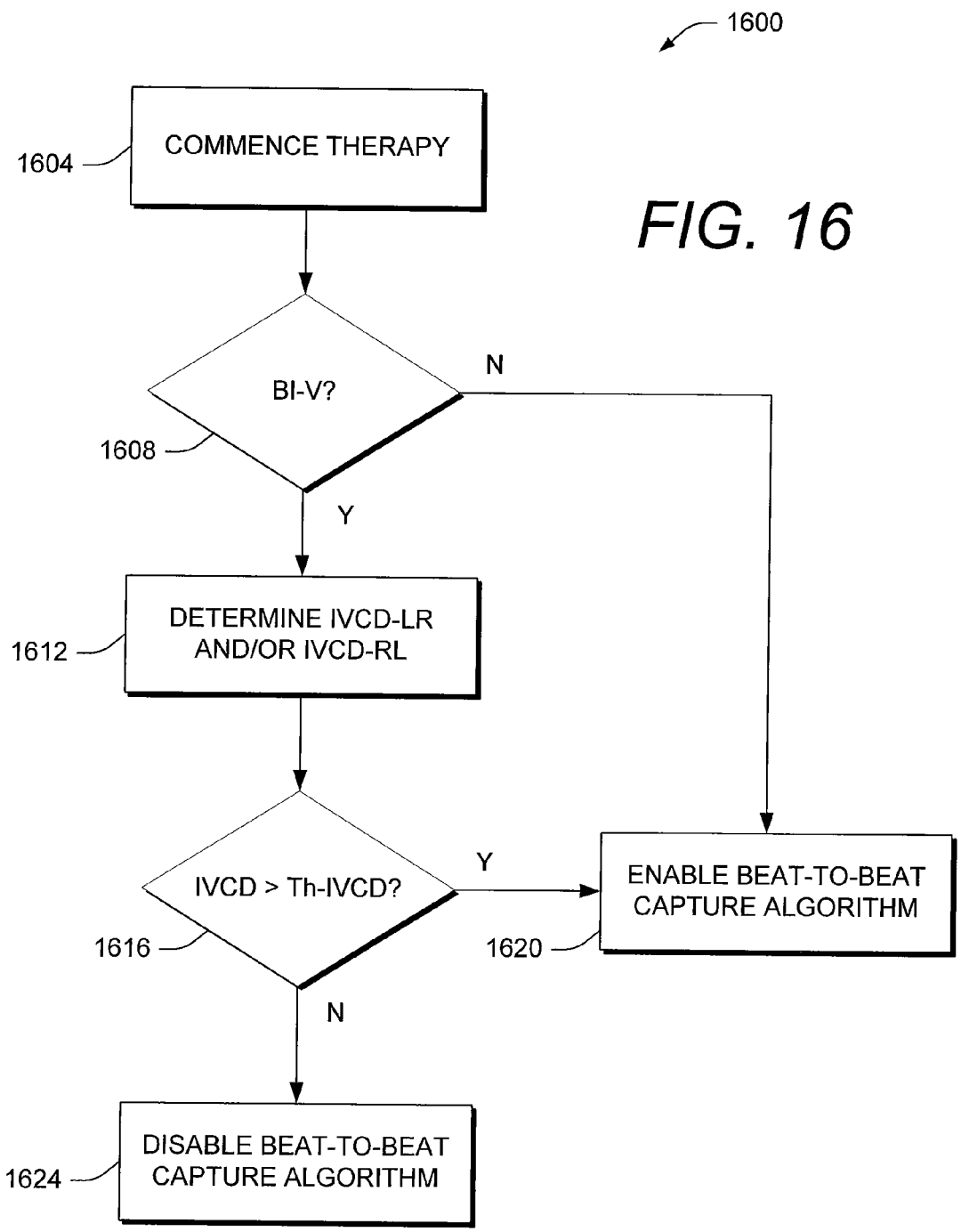
FIG. 16 is a flow chart of an exemplary method for deciding whether to enable or disable beat-to-beat capture detection based on an interval (e.g., IVCD).

FIG. 16 shows an exemplary method 1600 for deciding whether to enable or disable a beat-to-beat capture detection algorithm. A commencement block 1604 commences a pacing therapy. A decision block 1608 decides whether the therapy calls for bi-ventricular pacing. If the decision block 1608 decides that bi-ventricular pacing is not called for, i.e., being used, then the method 1600 enables a beat-to-beat capture detection algorithm. However, if the decision block 1608 decides that a bi-ventricular pacing therapy is being used, then the method 1600 proceeds to a determination block 1612 that determines IVCD-RL and/or IVCD-RL, for example, via measurement or recall of a stored value. The method 1600 continues at another decision block 1616 that decides if the IVCD value(s) is greater than a threshold(s). If the decision block 1616 decides that the IVCD value(s) is greater than the threshold, then, per the enablement block 1620, the beat-to-beat capture algorithm is enabled. Otherwise, the method 1600 continues at a disablement block 1624 that disables the beat-to-beat capture algorithm or otherwise ensures that the beat-to-beat capture algorithm is not enabled.

Thus, according to FIG. 16, an exemplary method may includes implementing a cardiac pacing therapy capable of delivering bi-ventricular stimulation, deciding if the therapy calls for bi-ventricular stimulation and, if the therapy calls for bi-ventricular stimulation, comparing an interventricular conduction delay to a threshold and based on the comparing, deciding whether to enable a beat-to-beat capture detection algorithm. In turn, the method may call for enabling or disabling or actually enable or disable a beat-to-beat capture detection algorithm.

Instructions (e.g., stored on a storage medium) may cause a processor to receive a IVCD-LR value and/or a IVCD-RL value and compare such value or values to one or more thresholds. Based on such a comparison, the processor may initiate an action (e.g., call a method, a function, set a flag, etc.). For example, the processor may set a flag or other indicator that enables or disables a capture algorithm, which may be performed by the processor. Such exemplary instructions (e.g., stored on a storage medium) can thereby render a result that can be useful for any of a variety of pacing devices or pacing systems.

Figure 17:
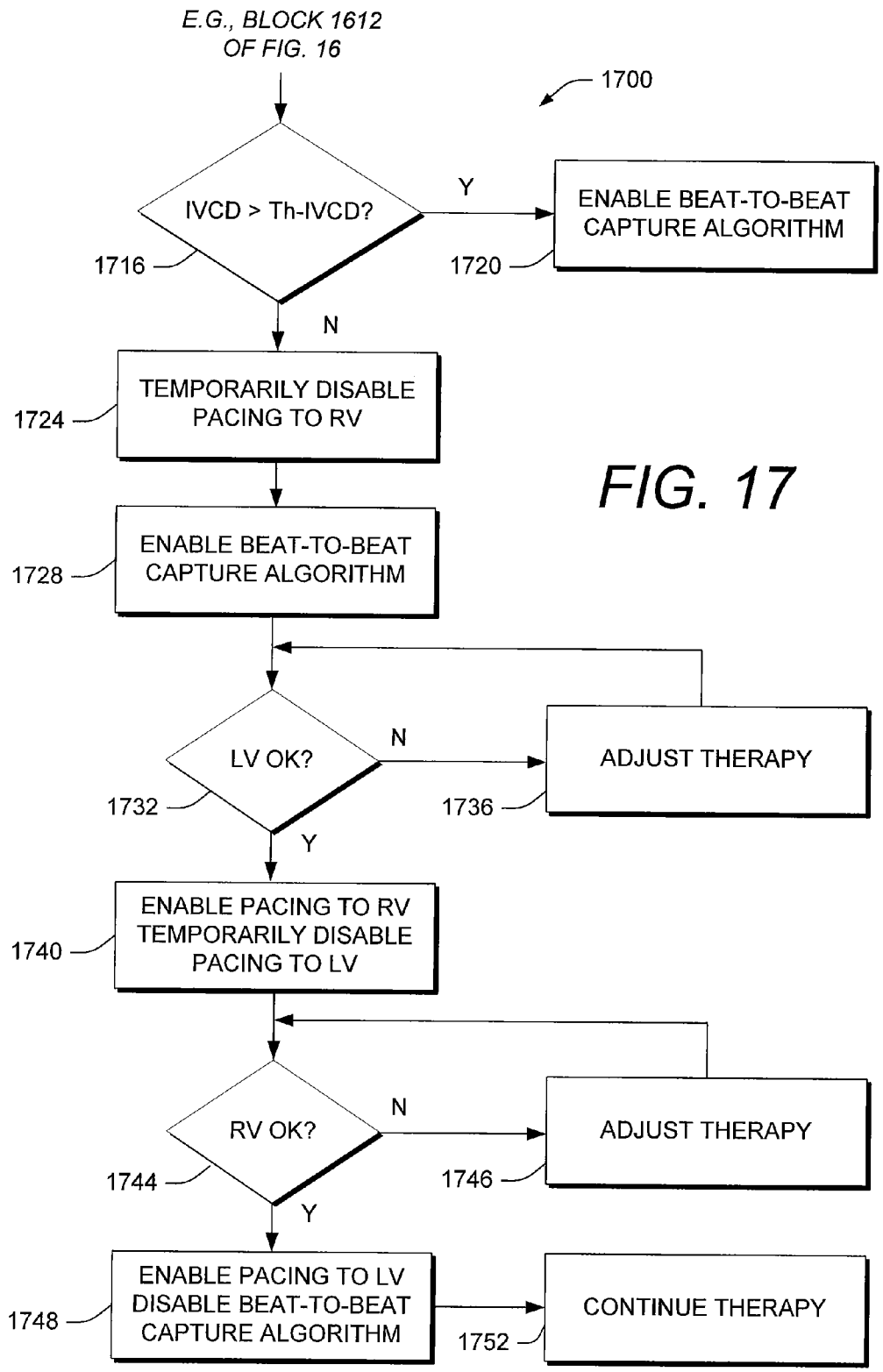
FIG. 17 is a flow chart of an exemplary method for deciding to temporarily disable pacing to a ventricle for purposes of capture assessment in the other ventricle.

FIG. 17 shows an exemplary method 1700 that may follow the determination block 1612 of the method 1600 of FIG. 16. However, action blocks 1724-1752 of the method 1700 may be implemented in one or more other manners. As shown in FIG. 17, the method 1700 includes a decision block 1716 that decides if an IVCD value(s) is greater than a threshold(s). If the decision block 1716 decides that the IVCD value(s) is greater than the threshold, then, per the enablement block 1720, the beat-to-beat capture algorithm is enabled, which is the same process as the method 1600. However, if the decision block 1716 decides that the IVCD(s) is less than the threshold, then the method continues at a disablement block 1724 that temporarily disables pacing to the right ventricle (or left ventricle).

With pacing to one ventricle temporarily disabled, an enablement block 1728 enables a beat-to-beat capture algorithm for that ventricle. A decision block 1732 then decides if capture is OK for the left ventricle (or right ventricle). If the decision block 1732 decides that capture is not OK, then the method 1700 enters an adjustment block 1736 to adjust therapy, such as, adjust an amplitude, a pulse duration, etc. Such an adjustment may include a threshold search for the left ventricle. After the adjustment or during the adjustment, as appropriate, the method 1700 returns to the decision block 1732.

Once capture at the left ventricle is OK, per the decision block 1732, then an action block 1740 enables pacing to the right ventricle (or left ventricle) and temporarily disables pacing to the left ventricle (or right ventricle). A decision block 1744 follows for capture detection of the right ventricle (or left ventricle). If capture is not OK, then the method 1700 enters an adjustment block 1746, which may act as the adjustment block 1736. Once the decision block 1744 decides that capture for the right ventricle (or left ventricle) is OK, then the method 1700 continues in an action block 1748 that enables pacing to the left ventricle and that disables the beat-to-beat capture algorithm. The therapy continues at a continuation block 1752, which may then, as appropriate, delivery bi-ventricular pacing therapy.

Figure 18:
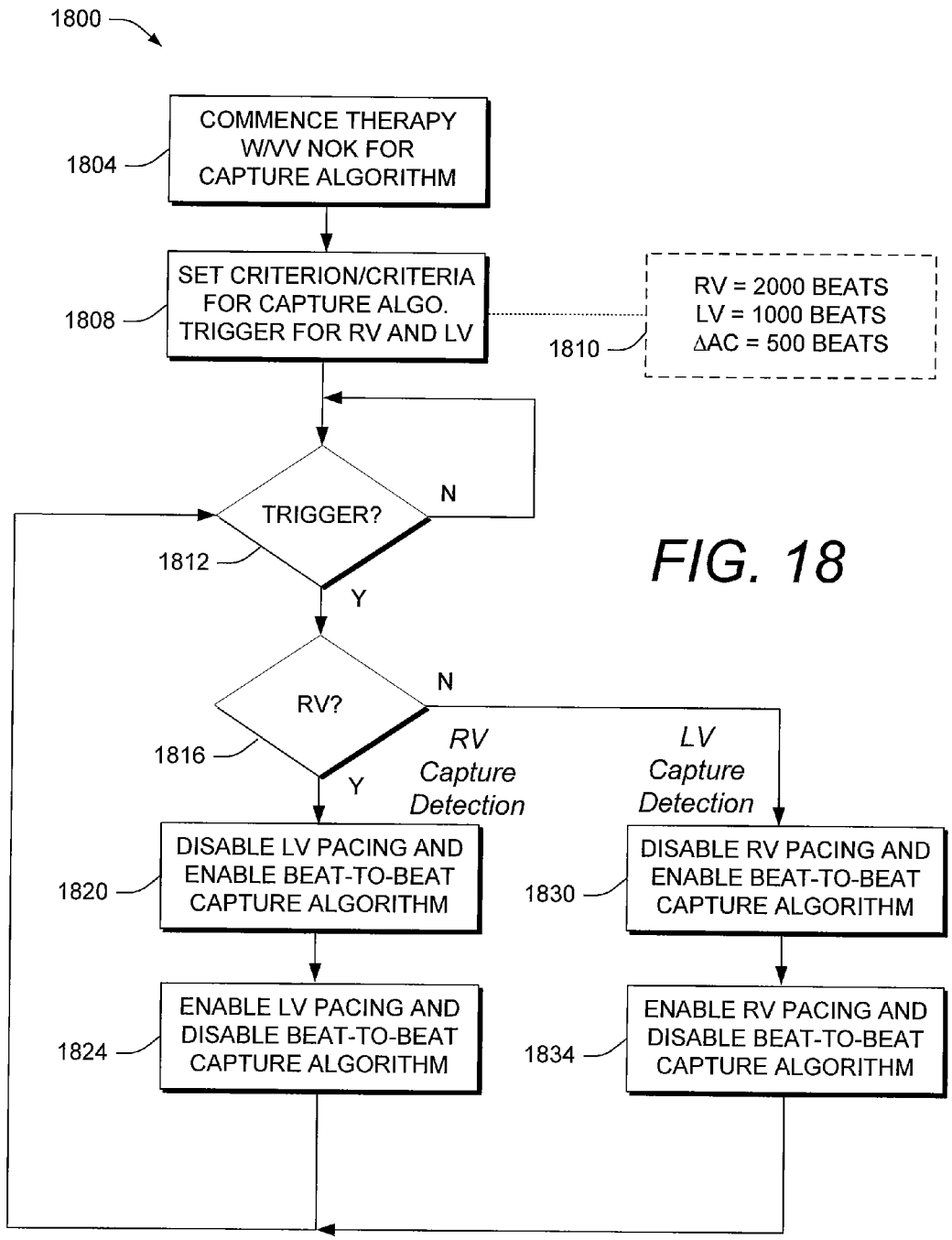
FIG. 18 is a flow chart of an exemplary method for setting one or more criteria for use in performing capture assessment for a ventricle.

FIG. 18 shows an exemplary method 1800 that may be implemented in instances where the bi-ventricular pacing parameter VV delay is deemed unsuitable for implementation of beat-to-beat capture detection. The method 1800 commences in block 1804 where a pacing therapy capable of delivering bi-ventricular pacing is administered to a patient using an implantable pacing device. The method 1800 continues in a set block 1806 where one or more criteria are set for implementation of a capture detection algorithm. The one or more criteria may pertain to right ventricular capture detection, left ventricular capture detection or both right and left ventricular capture detection. In the example of FIG. 18, a block 1810 indicates that an RV criterion triggers right ventricular capture detection every 2000 beats (e.g., about every 30 minutes) while a LV criterion triggers left ventricular capture detection every 1000 beats (e.g., about every 15 minutes) where an offset ΔAC ensures that the two triggers do not occur simultaneously. For example, at 1000 beats, the LV criterion may trigger, followed by LV triggering at 2000 beats and then RV triggering at 2500 beats. A variety of techniques may be used to help ensure that a patient has pacing for at least one ventricle.

As shown in FIG. 18, the method 1800 enters a decision block 1812 that decides if a trigger occurred per the one or more criteria. If a trigger does not occur, then the method 1800 continues at the decision block 1812, for example, on a beat-by-beat or other basis. However, if a trigger occurs, then the method 1800 enters a decision block 1816 that decides if the trigger occurred for the right ventricle. This decision block determines whether a RV path for RV capture detection (blocks 1820, 1824) or an LV path for LV capture detection occurs. Again, the one or more criterion ensure that these two paths do not occur at the same time, as the VV delay and/or other pacing parameter has indicated that beat-to-beat capture detection for both ventricles with bi-ventricular pacing should not occur.

The RV path includes an action block 1820 that disables LV pacing (RV pacing only) and that enables beat-to-beat capture detection. Once adequate capture detection has occurred, for example, over a sufficient number of beats to ensure proper RV capture, then another action block 1824 enables LV pacing and disables beat-to-beat capture detection. Similarly, the LV path includes an action block 1830 that disables RV pacing (LV pacing only) and that enables beat-to-beat capture detection. Once adequate capture detection has occurred, for example, over a sufficient number of beats to ensure proper LV capture, then another action block 1834 enables RV pacing and disables beat-to-beat capture detection. After either path, the method 1800 continues at the trigger decision block 1812.

An exemplary method may include selecting a first electrode configuration for sensing right ventricular activation, selecting a second electrode configuration for sensing left ventricular activation, sensing activity of the right ventricle and activity of the left ventricle using the first electrode configuration and the second electrode configuration, respectively, determining an interval between the activity of the right ventricle and the left ventricle and, based on the interval, setting a criterion for performing right ventricular capture verification using the first electrode configuration and setting a criterion for performing left ventricular capture verification using the second electrode configuration. According to such a method, the interval may be an IVCD or other parameter. The criteria set may be criteria similar to those of block 1810 of the method 1800 (e.g., number of cardiac cycles). In the instance the interval value changes, then the method may change one or more of the criteria, which, depending on the nature of the change, may cause the method to enable beat-to-beat capture detection.

Figure 19:
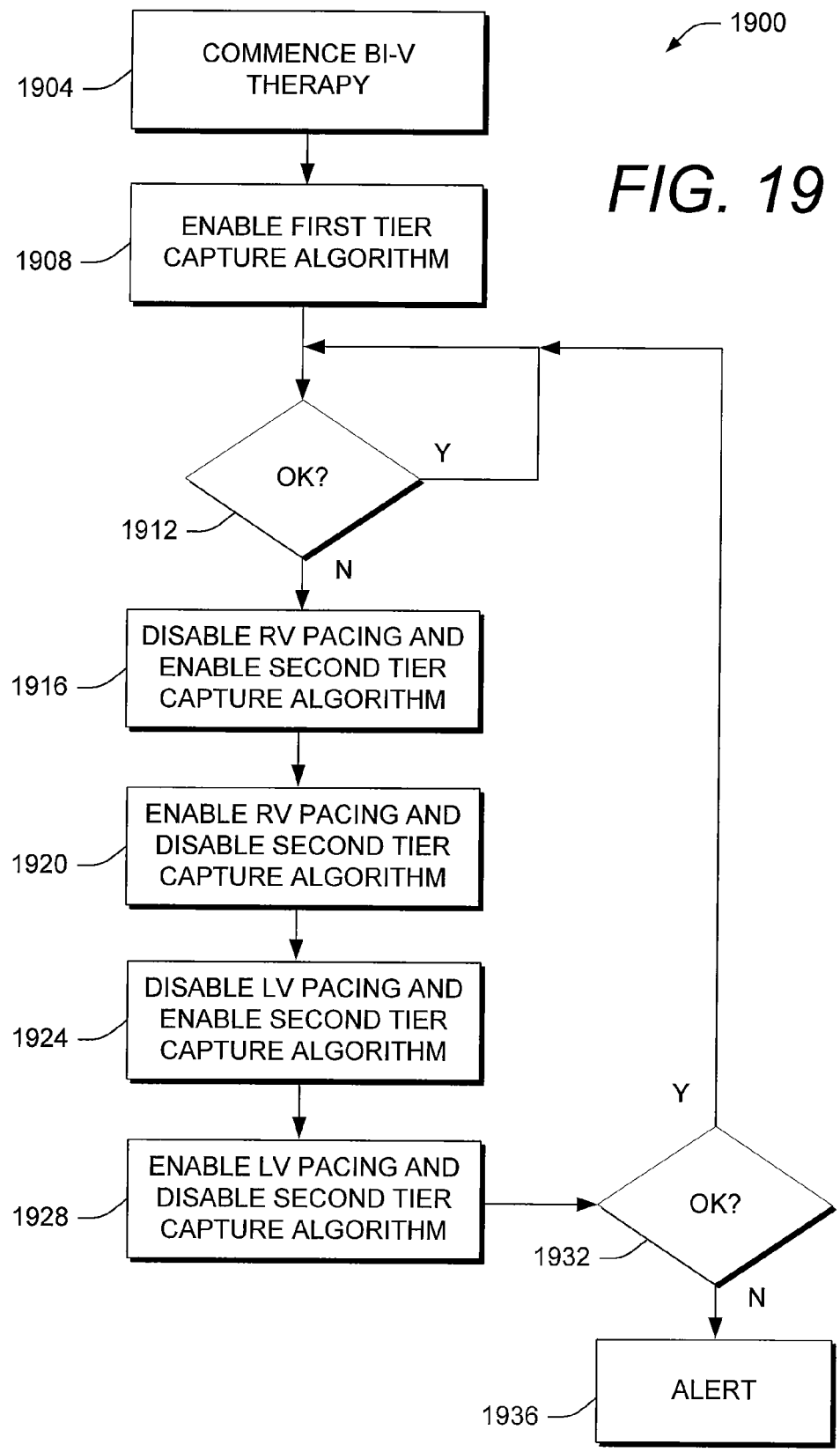
FIG. 19 is a flow chart of an exemplary method for implementing tiered capture detection.

FIG. 19 shows an exemplary method 1900 that uses tiered capture detection. A first tier provides a rough indication as to whether capture occurred for at least one ventricle while a second tier provides a more accurate capture assessment for a ventricle. Per the method 1900, such a tiered technique may be implemented based on an analysis of one or more pacing parameters. For example, if an IVCD, Δ or other parameter indicates that beat-to-beat capture detection may be confounded by fusion, then a tiered approach may be used.

In general, a first tier operates for bi-ventricular pacing while a higher tier operates for single ventricle pacing. A first tier may use one or more criteria to err on the side of indicating non-capture (or calling for a higher tier) when capture actually occurred. In addition, a first tier may be unsuitable for use in determining a capture threshold while a higher tier may be suitable for determining a capture threshold.

The method 1900 commences in a therapy block 1904 that implements a bi-ventricular pacing therapy (e.g., CRT). An enablement block 1908 enables a first tier of capture detection that can operate during periods of bi-ventricular pacing. Such first tier capture detection algorithm may rely on an amplitude limit where sensed cardiac activity in excess of the limit indicates that at least one ventricle captured or conversely, an amplitude at or below the limit indicates that no capture occurred or perhaps that fusion may exist. A decision block 1912 decides whether capture is present, optionally without regard to, specifically, capture occurred in the RV, the LV or both RV and LV.

In the instance that the decision block 1912, per the first tier, decides that capture did not occur or that a question or uncertainty exists that capture did not occur, then the method 1900 enters a disablement block 1916 that disables RV pacing and enables a second tier capture detection algorithm to investigate LV capture. Once the method 1900 has investigated LV capture, an enablement block 1920 enables RV pacing and disables the second tier capture detection algorithm, as the method 1900 returns to bi-ventricular pacing.

The method 1900 may continue at the first tier block 1908 or at another appropriate point. However, in the example of FIG. 19, the method 1900 continues with an investigation of RV capture, per the disablement block 1924, which disables LV pacing and enables a second tier capture detection algorithm. Once the method 1900 has investigated LV capture, an enablement block 1928 enables LV pacing and disables the second tier capture detection algorithm, as the method 1900 returns to bi-ventricular pacing.

After checks for RV capture and LV capture, the method 1900 enters a decision block 1932 that decides if RV and LV capture are OK, for example, according to feedback that capture was attained for both ventricles. If the decision block 1932 decides that capture was attained for both ventricles, then the method continues with first tier capture detection, otherwise, the method 1900 may issue an alert per the alert block 1936.

An exemplary method includes selecting a first electrode configuration for sensing right ventricular activation, selecting a second electrode configuration for sensing left ventricular activation, sensing activity of the right ventricle and activity of the left ventricle using the first electrode configuration and the second electrode configuration, respectively, determining an interval between the activity of the right ventricle and the left ventricle and, based on the interval, deciding whether to use a tiered capture verification scheme (see, e.g., the first and second tier of the method 1900). According to such a method, the interval may be an IVCD or other parameter.

Figure 20:
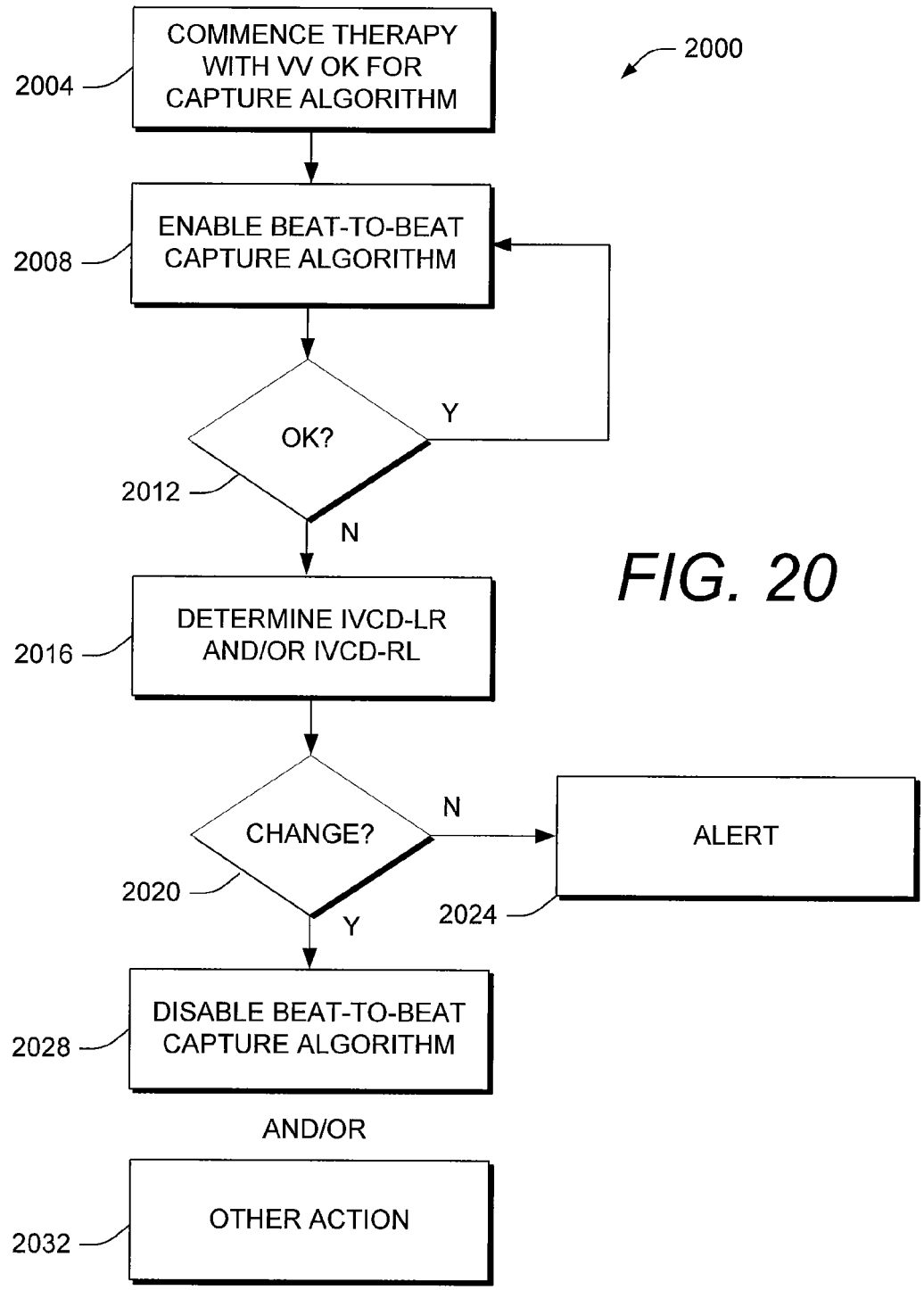
FIG. 20 is a flow chart of an exemplary method for deciding whether a change occurred in circumstances, such as, a change in an interventricular conduction interval, and for responding to such a change.

FIG. 20 shows an exemplary method 2000 that monitors an interval such as the IVCD interval to decide whether a change has occurred that warrants further action. The method 2000 commences in a therapy delivery block 2004 that delivers a therapy where the VV delay is deemed suitable for implementation of beat-to-beat capture detection (see, e.g., the exemplary method 2100 of FIG. 21). Based on the interval value, an enablement block 2008 enables beat-to-beat capture detection.

While beat-to-beat capture detection is implemented, a decision block 2012 decides if performance is adequate. For example, if the algorithm performs reliably without instance of searching for a capture threshold that is approximately the same as a previous capture threshold, which may indicate that a loss of capture was due to sensing or fusion issues, then the decision block 2012 may decide that the beat-to-beat capture detection algorithm is performing OK and continue at the enablement block 2008 or other appropriate point.

However, if the decision block 2012 decides that the beat-to-beat capture detection algorithm is experiencing problems, then the method 2000 continues at a determination block 2016 that determines an IVCD value or values (e.g., IVCD-RL, IVCD-LR). A decision block 2020 follows that decides if the interval(s) changed with respect to a prior determined value(s). If no change has occurred, then the method 2000 continues at an alert block 2024, which issues an alert that capture issues exist where such issues are not due to a change in an IVCD. However, if a change has occurred, then the method 2000 continues along another path to further investigate the consequences and/or possible solutions that address the change in the IVCD(s).

Disablement block 2028 disables beat-to-beat capture detection as the decision block 2012 indicated that it was performing unreliably. An "other" action block 2032 may call for one or more other actions in addition to disabling the beat-to-beat capture detection or as alternatives to such disabling.

An exemplary method may include enabling a beat-to-beat capture detection algorithm, detecting loss of capture to one or both ventricles using the capture detection algorithm, in response to the detecting loss of capture, determining an interval between activity of the right ventricle and activity of the left ventricle, comparing the interval to a threshold and, based on the comparing, deciding whether to disable the beat-to-beat capture detection algorithm. Such a method may initiate or call for disabling the beat-to-beat capture detection algorithm and may actually disable it.

According to this example, the threshold may be a prior interval value. For example, the interval may be an IVCD-RL or IVCD-LR value for a particular time that is compared to an IVCD-RL or IVCD-LR for a prior time. An exemplary method may track such interval values over time and indicate whether a trend exists where a decision may need to be made with respect to use of capture detection, especially beat-to-beat capture detection for bi-ventricular pacing therapy.

An exemplary method may determine a threshold value for use in deciding whether to enable bi-ventricular beat-to-beat capture detection or in deciding whether to disable such capture detection. Such a method may use a measured pacing latency for one or both ventricles. Thus, a threshold may depend at least in part on a pacing latency value (e.g., a time of about 50 ms, etc.).

FIG. 21 shows an exemplary method 2100 that compares the parameter VV to one or more criteria to determine whether to enable or disable a bi-ventricular beat-to-beat capture detection algorithm. A determination block 2104 determines VV for bi-ventricular pacing therapy. The parameter VV may be determined in any of a variety of manners. FIG. 21 shows an example in block 2106, which has already been described above. A decision block 2108 compares VV to a threshold (Th-VV). The threshold (Th-VV) may be determined in any of a variety of manners. FIG. 21 shows an example in block 2110, which has already been described above.

If the decision block 2108 decides that VV is less than the threshold (Th-VV), then the risk of fusion interfering with capture detection is deemed minimal or non-existent and an action block 2112 enables the bi-ventricular beat-to-beat capture detection algorithm. For example, the VV is short and thus allows little time for a conducted wavefront to cause fusion. However, if the parameter VV equals or exceeds the threshold (Th-VV), then an action block 2116 disables the bi-ventricular beat-to-beat capture detection algorithm. In general, an increase in VV allows more time for wavefronts to fuse.

Scenarios may exist where a change in VV occurs that could increase risk of fusion and hence render a bi-ventricular beat-to-beat capture detection algorithm problematic. Alternatively, a change may occur that decreases risk of fusion and hence allow a disabled capture detection algorithm to be enabled. An exemplary method may call for a method such as the method 2100 after a change in VV or during an update to VV (e.g., during execution of a VV determination algorithm).

Referring to the determination block 2104 and the block 2106, an exemplary method may include implanting an electrode in a position for delivering energy to activate the right ventricle, implanting an electrode in a position for delivering energy to activate the left ventricle, determining an interval (e.g., an IVCD) by delivering energy to activate the right or left ventricle and sensing activity in the left or the right ventricle, respectively, wherein the sensed activity is related to the delivered energy and based at least in part on the interval, determining an interventricular delay (e.g., VV delay) for delivery of a bi-ventricular pacing therapy that allows for bi-ventricular capture detection. Such a method may include use of a pacing latency (e.g., PL) and/or a time parameter (e.g., −2*RS). As an example, the time parameter may be approximately 40 ms.

Figure 22:
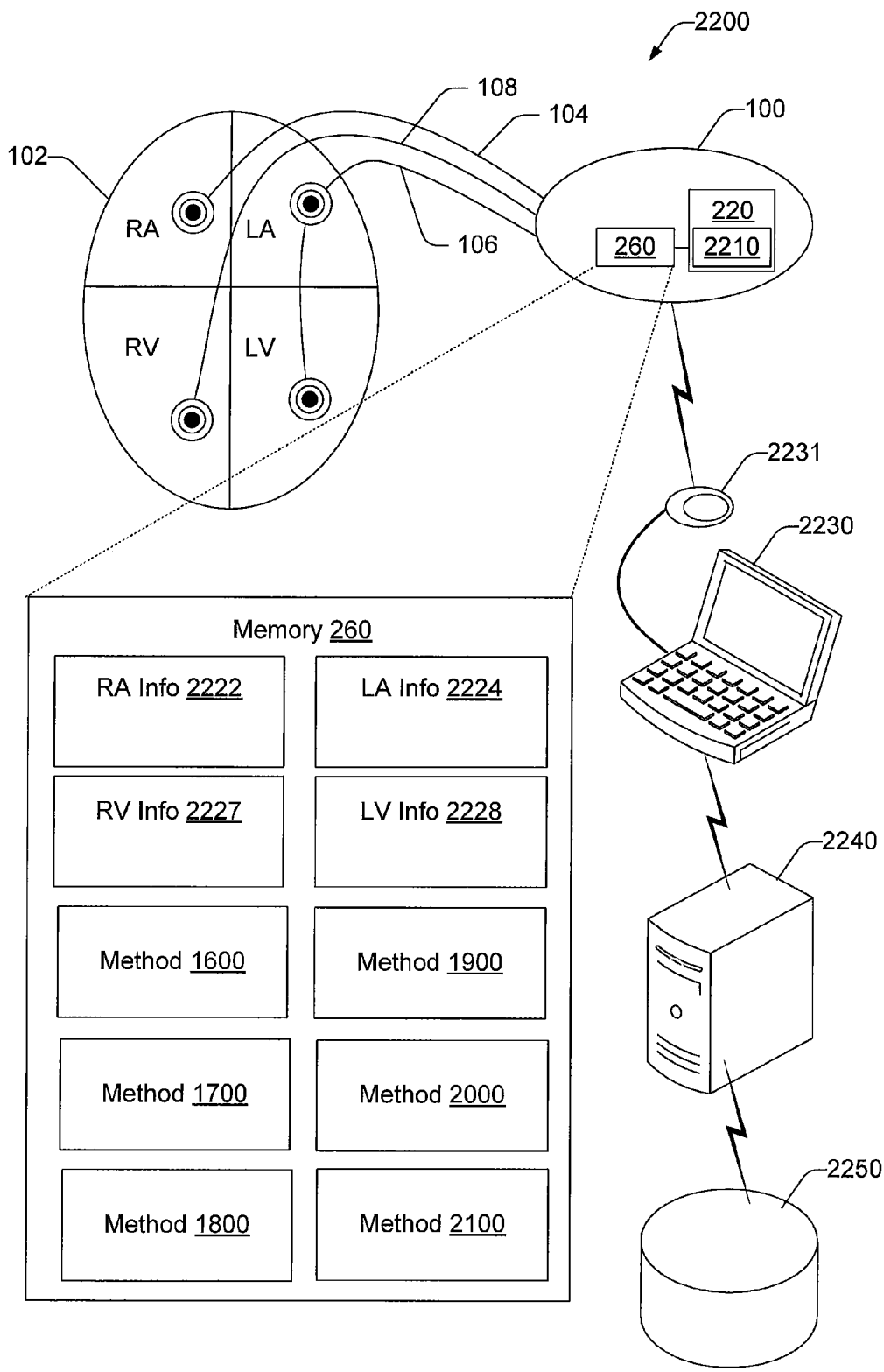
FIG. 22 is a diagram of an exemplary system for use in implementing various exemplary techniques.

FIG. 22 shows an exemplary system 2200 that includes the exemplary implantable device 100 of FIGS. 1 and 2, with processor 220 including one or more modules 2210, for example, that may be loaded via memory 260. A series of leads 104, 106 and 108 provide for delivery of stimulation energy and/or sensing of cardiac activity, etc., associated with the heart 102. Stylized bullets indicate approximate positions or functionality associated with each of the leads 104, 106 and 108. Other arrangements are possible as well as use of other types of sensors, electrodes, etc.

Memory 260 is shown as including RA information 2222, LA information 2224, RV information 2227 and LV information 2228. Such information may include one or more pacing parameters, historical interval values, etc. Memory 260 also include appropriate modules (e.g., processor-executable instructions) for performing various actions of the methods 1600-2100, noting that part of a method may be performed using a device other than the implantable device 100.

The system 2200 includes a device programmer 2230 having a telemetry unit 2231 for communicating with the implantable device 100. The programmer 2230 may further include communication circuitry for communication with another computing device 2240, which may be a server. The computing device 2240 may be configured to access one or more data stores 2250, for example, such as a database of information germane to a patient, an implantable device, therapies, etc.

CONCLUSION

Although exemplary methods, devices and/or systems have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices and/or systems.

What is claimed is:

1. A method comprising:
   implementing a bi-ventricular cardiac pacing therapy;
   delivering energy to activate the right or left ventricle;
   measuring a paced or a sensed interventricular conduction delay from the paced left or right ventricle to the opposing non-paced left or right ventricle; and
   comparing the measured paced or sensed interventricular conduction delay to a threshold and based on the comparing, deciding whether to perform a capture detection algorithm for the bi-ventricular cardiac pacing therapy.

2. The method of claim 1 wherein the interventricular conduction delay comprises a paced interventricular conduction delay measured by delivering energy to one ventricle and sensing electrical activity related to the delivered energy in the other ventricle.

3. The method of claim 1 wherein the interventricular conduction delay comprises a sensed interventricular conduction delay measured by sensing electrical activity in one ventricle for contraction of that ventricle and sensing electrical activity related to the contraction in the other ventricle.

4. The method of claim 1 further comprising enabling the capture detection algorithm if the interventricular conduction delay exceeds the threshold.

5. The method of claim 1 further comprising disabling the capture detection algorithm if the interventricular conduction delay does not exceed the threshold.

6. The method of claim 1 further comprising temporarily disabling pacing to the right ventricle, enabling a capture detection algorithm for the left, delivering energy to the left ventricle and deciding whether the energy captured the left ventricle.

7. The method of claim 1 further comprising temporarily disabling pacing to the left ventricle, enabling a capture detection algorithm for the right ventricle, delivering energy to the right ventricle and deciding whether the energy captured the right ventricle.

8. A method comprising:
   implanting an electrode in a position for delivering energy to activate the right ventricle;
   implanting an electrode in a position for delivering energy to activate the left ventricle;
   determining an interval by delivering energy to activate the right or left ventricle and sensing activity in the non-paced opposing left or the right ventricle, respectively, wherein the sensed activity is related to the delivered energy;
   based on the interval, deciding whether the electrode positions are suitable for performing capture verification.

9. The method of claim 8 wherein the performing capture verification comprises performing capture verification for bi-ventricular pacing.

10. The method of claim 8 wherein the interval comprises an interventricular conduction interval.

11. The method of claim 8 wherein the deciding comprises comparing the interval to a threshold.

12. The method of claim 8 further comprising temporarily disabling delivery of energy to one of the ventricles, enabling a capture detection algorithm for the other ventricle, delivering energy to the other ventricle and deciding whether the energy captured the other ventricle.

13. A method comprising:
   determining an interval by delivering energy to activate the right or left ventricle and sensing activity in the non-paced opposing left or the right ventricle, respectively, wherein the sensed activity is related to the delivered energy; and
   based at least in part on the interval, determining an interventricular delay for delivery of a bi-ventricular pacing therapy that allows for bi-ventricular capture detection.

14. The method of claim 13 wherein the determining further comprises using a pacing latency.

15. The method of claim 14 wherein the determining determines the interventricular delay as the interval minus the pacing latency minus a time parameter.

16. An implantable device comprising:
   a power source;
   a processor;
   memory; and
   control logic to call for delivery of energy to activate the right or left ventricle and the acquisition of a paced or a sensed interventricular conduction delay from the paced left or right ventricle to the non-paced opposing left or right ventricle and to enable or disable a capture detection algorithm based on a comparison of an acquired paced or a sensed interventricular conduction delay to a threshold.

17. An implantable device comprising:
   a power source;
   a processor;
   memory; and
   control logic to determine an interval by delivering energy to activate the right or left ventricle and sensing activity in the non-paced opposing left or the right ventricle, respectively, wherein the sensed activity is related to the delivered energy and to determine an interventricular delay for delivery of a bi-ventricular pacing therapy that allows for bi-ventricular capture detection wherein the determination is based at least in part on the interval.

* * * * *